United States Patent
Dowle et al.

(10) Patent No.: US 7,157,494 B2
(45) Date of Patent: Jan. 2, 2007

(54) DIMERIC COMPOUNDS AND THEIR USE AS ANTI-VIRAL AGENTS

(75) Inventors: Michael D. Dowle, Stevenage (GB); Betty Jin, Mount Waverley (AU); Simon J. F. Macdonald, Stevenage (GB); Andrew McM Mason, Stevenage (GB); Darryl McConnell, Vienna (AT); Van T. T. Nguyen, Noble Park (AU); Stephen E. Shanahan, Stevenage (GB); Wen-Yang Wu, Mount Waverley (AU)

(73) Assignee: Biota Scientific Management Pty. Ltd., Victoria (AU)

( * ) Notice: Subject to any disclaimer, the term of this patent is extended or adjusted under 35 U.S.C. 154(b) by 52 days.

(21) Appl. No.: 10/494,243

(22) PCT Filed: Nov. 8, 2002

(86) PCT No.: PCT/AU02/01524

§ 371 (c)(1),
(2), (4) Date: Nov. 1, 2004

(87) PCT Pub. No.: WO03/040135

PCT Pub. Date: May 15, 2003

(65) Prior Publication Data

US 2005/0038108 A1    Feb. 17, 2005

(30) Foreign Application Priority Data

Nov. 9, 2001    (AU) .................................. PR8798
May 27, 2002    (AU) .................................. PS2600

(51) Int. Cl.
*A61K 31/35*    (2006.01)

(52) U.S. Cl. .................. 514/459; 549/424; 549/425

(58) Field of Classification Search ............. 514/459; 549/424, 425
See application file for complete search history.

(56) References Cited

U.S. PATENT DOCUMENTS 6,548,476 B1 * 4/2003 Wu et al. ..................... 514/2

FOREIGN PATENT DOCUMENTS

WO    WO 00/55149 A1    9/2000
WO    WO 02/20514 A1    3/2002

OTHER PUBLICATIONS

McDonald, SJF et al 'Dimeric zanamivir conjugates with various linking groups are potent, long-lasting inhibitors of influena neuraminidase including H5n1 avian' CA 142:423048 (2005).*
Fleming, DM 'Managing influenza: amantadine, rimantadine and beyond' PMID: 11351773 (2001).*

* cited by examiner

*Primary Examiner*—Amelia A. Owens
(74) *Attorney, Agent, or Firm*—Foley & Lardner LLP

(57) ABSTRACT

The invention relates to compounds of general formula (I); in which R is an amino or guanidino group; $R^2$ is acetyl or trifluoroacetyl; X is CONH, $SO_2NH$, NHCO or NHCONH; m is either 0 or 1; n is an integer from 2 to 6; q is an integer from 0 to 3; and Y is hydrogen or an aromatic substituent, or a pharmaceutically acceptable derivative thereof; methods for their preparation, pharmaceutical formulations containing them or their use in the prevention or treatment of a viral infection

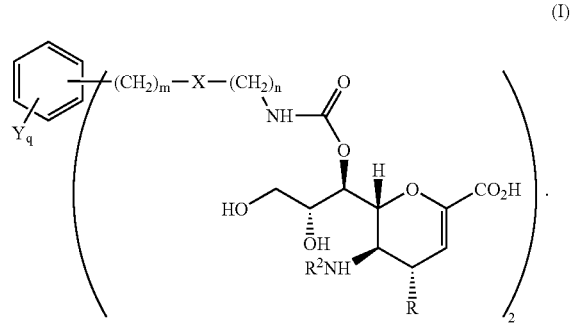

20 Claims, No Drawings

DIMERIC COMPOUNDS AND THEIR USE AS ANTI-VIRAL AGENTS

This invention relates to new chemical compounds and their use in medicine. In particular the invention concerns novel dimeric compounds, methods for their preparation, pharmaceutical formulations thereof and their use as anti-viral agents.

BACKGROUND OF THE INVENTION

Enzymes with the ability to cleave N-acetyl neuraminic acid (NANA), also known as sialic acid, from other carbohydrates are present in many microorganisms. These include bacteria such as *Vibrio cholerae, Clostridium perfringens, Streptococcus pneumoniae* and *Arthrobacter sialophilus*, and viruses such as influenza virus, parainfluenza virus, mumps virus, Newcastle disease virus and Sendai virus. Most of these viruses are of the orthomyxovirus or paramyxovirus groups, and carry a neuramimidase activity on the surface of the virus particles. Many of these neuramimidase-possessing organisms are major pathogens of man and/or animals, and some, such as influenza virus and Newcastle disease virus, cause diseases of enormous importance.

It has long been thought that inhibitors of neuramimidase might prevent infection by neuramimidase-bearing viruses. Most of the known neuramimidase inhibitors are analogues of neuraminic acid, such as 2-deoxy-2,3-dehydro-N-acetylneuraminic acid (DANA) and some of its derivatives (Meindl et al, Virology, 1974 58 457). Our International Patent Publication No. WO 91/16320 describes a number of analogues of DANA which are active against viral neuramimidase, and it has been shown in particular that 4-guanidino-2-deoxy-2,3-dehydro-N-acetylneuraminic acid (Compound (A), code number GG167) is useful in the treatment of influenza A and B (N. Engl. J. Med., 1997 337 874–880). Other patent applications describe various closely-related sialic acid derivatives (eg. PCT Publications No. WO 95/18800, No. WO 95/20583 and No. WO 98/06712), and anti-viral macromolecular conjugates of GG167 have also been described (International Patent Application No. PCT/AU97/00771).

Compound (A)

International Patent Publication No. WO 00/55149, describes dimeric compounds which comprise two neuramimidase binding molecules, such as compound (A), attached to a common spacer or linking group of up to 100 atoms in length.

We have now discovered a novel class of compounds which fall within the generic scope of International Patent Publication No. WO 00/55149, but which are not specifically disclosed therein, and exhibit a surprisingly advantageous anti-influenza activity profile which includes a long lung residency time and high potency.

Without wishing to be bound by theory, the basis for the long residency time in the lungs is thought to be due to the size and molecular weight of the compounds preventing entry through tight junctions in the respiratory epithelium and the polarity of the compounds being such that passage through the cell membranes occurs very inefficiently. An alternative theory is that the compounds themselves interact with the phospholipids in the cell membrane or other components of the respiratory epithelium and increase the residency time in the lungs.

SUMMARY OF THE INVENTION

In a first aspect, the present invention provides for a compound of general formula (I):

(I)

in which

R is an amino or guanidino group;
$R^2$ is acetyl or trifluoroacetyl;
X is CONH, $SO_2NH$, NHCO or NHCONH;
m is either 0 or 1;
n is an integer from 2 to 6;
q is an integer from 0 to 3; and
Y is hydrogen or an aromatic substituent,
or a pharmaceutically acceptable derivative thereof.

Preferably R is a guanidino group.
Preferably $R^2$ is an acetyl group.

Suitable aromatic substituents include alkyl, alkenyl, alkynyl, aryl, halo, haloalkyl, haloalkenyl, haloalkynyl, haloaryl, hydroxy, alkoxy, alkenyloxy, aryloxy, carboxy, benzyloxy, haloalkoxy, haloalkenyloxy, haloaryloxy, nitro, azido, amino, alkylamino, alkenylamino, alkynylamino, arylamino, benzylamino, acylamino, acyl, arylacyl, acylamino, acyloxy, alkylsulphonyl, arylsulphonyl, sulphonylamino, alkylsulphonylamino, arylsulphonylamino, heterocyclyl, heterocycloxy, heterocyclylamino, haloheterocyclyl, mercapto, sulfonic acid, alkylthio, arylthio and acylthio.

Preferably the alkyl, alkenyl, alkynyl and alkoxy substituents contain up to 6 carbon atoms.

More preferably Y is hydrogen, halogen, $C_{1-4}$ alkyl, hydroxy, $C_{1-4}$ alkoxy, amino or carboxy.

It will be appreciated by those skilled in the art that the compounds of formula (I) may be modified to provide pharmaceutically acceptable derivatives thereof at any one or more of the functional groups in the compounds of formula (I). Of particular interest as such derivatives are compounds modified at the carboxyl function, hydroxyl functions or at amino groups. Thus compounds of interest include alkyl esters, such as methyl, ethyl, propyl or isopropyl esters, aryl esters, such as phenyl, benzoyl esters, and acetyl esters of the compounds of formula (I).

The term "pharmaceutically acceptable derivative" means any pharmaceutically acceptable salt, ether, ester or salt of such ester of a compound of formula (I) or any other compound which, upon administration to the recipient, is capable of providing a compound of formula (I) or an anti-virally active metabolite or residue thereof. Of particular interest as derivatives are compounds modified at the sialic acid carboxy or glycerol hydroxy groups, or at amino and guanidine groups.

Pharmaceutically acceptable salts of the compounds of formula (I) include those derived from pharmaceutically acceptable inorganic and organic acids and bases. Examples of suitable acids include hydrochloric, hydrobromic, sulphuric, nitric, perchloric, fumaric, maleic, phosphoric, glycollic, lactic, salicylic, succinic, toluene-p-sulphonic, tartaric, acetic, citric, methanesulphonic, formic, benzoic, malonic, naphthalene-2-sulphonic and benzenesulphonic acids. Other acids such as oxalic acid, while not in themselves pharmaceutically acceptable, may be useful in the preparation of salts useful as intermediates in obtaining compounds of the invention and their pharmaceutically acceptable acid addition salts.

Salts derived from appropriate bases include alkali metal (eg. sodium), alkaline earth metal (eg. magnesium), ammonium, and $NR_4^+$ (where R is $C_{1-4}$alkyl) salts.

The compounds of the invention may be prepared by methods described herein. It will be apparent to those skilled in the art, that it is necessary to use protecting groups to protect one or more functional groups of the neuramimidase binding molecule during the process of attaching the monomers to the alkyl spacer group. See for example "Protective Groups in Organic Synthesis" by T. W. Green and P. G. M. Nuts (John Wiley & Sons, 1991). Pharmaceutically acceptable salts of the compounds of formula (I) may be prepared according to known procedures.

For ease of processing and preparation, it is preferable that the compounds of formula (I) are in crystalline form.

Accordingly, the present invention also provides a method for the preparation of the compound of formula (I) as defined above, which comprises the step of deprotecting a compound of formula (II)

(II)

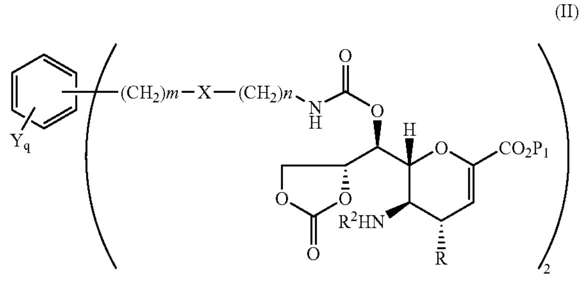

in which R and $R^2$ are as defined above and $P_1$ is a carboxylic acid protecting group.

The compounds of formula (I) possess antiviral activity. In particular these compounds are inhibitors of viral neuramimidase of orthomyxoviruses and paramyxoviruses, for example the viral neuramimidase of influenza A and B, parainfluenza, mumps and Newcastle disease.

Thus in a second aspect the invention provides a compound of formula (I) or a pharmaceutically acceptable derivative thereof, for use as an active therapeutic agent in the treatment of a viral infection, for example orthomyxovirus and paramyxovirus infections.

In a third aspect the invention provides a method for the prevention or treatment of a viral infection comprising the step of administration to a subject in need thereof of an effective amount of a compound of formula (I), or a pharmaceutically acceptable salt or derivative thereof.

Preferably, the viral infection is an orthomyxovirus or paramyxovirus infection. More preferably the viral infection is an influenza A or B infection.

Preferably the subject is an animal such as a mammal, more preferably a human, or a member of the genus *Equus*, for example a horse, donkey or mule. Most preferably the mammal is a human.

In a fourth aspect the invention provides use of a compound of the invention for the manufacture of a medicament for the treatment of a viral infection.

As used herein, the term "effective amount" is meant an amount of the compound of formula I effective to preventing or treating a viral infection in order to yield a desired therapeutic response. For example, to overcome or alleviate the effects of a viral infection.

The term "therapeutically-effective amount" means an amount of the compound of formula I to yield a desired therapeutic response. For example, treating or preventing a viral infection.

The specific "therapeutically-effective amount" will, obviously, vary with such factors as the particular viral infection being treated, the physical condition of the subject, the type of animal being treated, the duration of the treatment, the nature of concurrent therapy (if any), and the specific formulation employed and the structure of the compound or its derivatives.

Generally, the terms "treating", "treatment" and the like are used herein to mean affecting a subject, tissue or cell to obtain a desired pharmacologic and/or physiologic effect. The effect may be prophylactic in terms of completely or partially preventing a viral infection or sign or symptom thereof, and/or may be therapeutic in terms of a partial or complete cure of a viral infection. "Treating" as used herein covers any treatment of, or prevention of a viral infection in a vertebrate, a mammal, particularly a human, and includes: (a) preventing the viral infection from occurring in a subject that may be predisposed to the viral infection, but has not yet been diagnosed to the viral infection, but has not yet been diagnosed as having it; (b) inhibiting the viral infection, ie., arresting its development; or (c) relieving or ameliorating the effects, i.e., cause regression of the symptoms of the viral infection.

The compounds of the invention may also be used in diagnostic methods, in particular methods for the detection of influenza virus. For use in such methods it may be advantageous to link a compound of the invention to a label, such as a radioactive, fluorescent or chemiluminescent label.

Methods of diagnosis for which the compounds of the invention are suitable are described, for example, in our earlier applications PCT/AU97/00109 and PCT/AU97/00771.

In a fifth aspect the invention provides a method for the detection of a viral infection which comprises the step of contacting the compound of the invention with a sample suspected of containing the virus.

It will be further appreciated that the amount of a compound of the invention required for use in treatment will vary not only with the particular compound selected but also with the route of administration, the nature of the condition being treated, and the age and condition of the patient, and will ultimately be at the discretion of the attendant physician or veterinarian. In general however, a suitable dose will be in the range of from about 0.001 to 100 mg/kg of bodyweight per day, preferably in the range of 0.01 to 10 mg/kg/day, most preferably in the range of 0.1 to 1 mg/kg/day.

Treatment is preferably commenced before or at the time of infection and continued until virus is no longer present in the respiratory tract. However the compounds are also effective when given post-infection, for example after the appearance of established symptoms.

Suitably treatment is given on one or two occasions, preferably only once only for treatment, and preferably once per week for prophylaxis.

The compound is conveniently administered in unit dosage form, for example containing 1 to 100 mg, more conveniently 1 to 20 mg of active ingredient per unit dosage form.

While it is possible that, for use in therapy, a compound of the invention may be administered as the raw chemical, it is preferable to present the active ingredient as a pharmaceutical formulation.

Thus in a sixth aspect the invention provides a pharmaceutical formulation comprising a compound of formula (I) or a pharmaceutically acceptable salt or derivative thereof, together with one or more pharmaceutically acceptable carriers therefor and, optionally, other therapeutic and/or prophylactic ingredients. The carrier(s) must be "acceptable" in the sense of being compatible with the other ingredients of the formulation and not being deleterious to the recipient thereof.

The compounds of the invention may also be used in combination with other therapeutic and/or prophylactic agents, for example other anti-infective agents. In particular the compounds of the invention may be employed with other antiviral agents. The invention thus provides in a seventh aspect a combination comprising a compound of formula (I) or a pharmaceutically acceptable salt or derivative thereof together with another therapeutically and/or prophylactically active agent, in particular an antiviral agent.

The combinations referred to above may conveniently be presented for use in the form of a pharmaceutical formulation and thus such formulations comprising a combination as defined above together with a pharmaceutically acceptable carrier therefor comprise a further aspect of the invention.

Suitable therapeutic and/or prophylactic agents for use in such combinations include other anti-infective agents, in particular anti-bacterial and anti-viral agents such as those used to treat respiratory infections. For example, other compounds or vaccines effective against influenza viruses, such as the sialic acid analogues referred to above, e.g. zanamivir, oseltamivir, amantadine, rimantadine and ribavirin and FluVax, may be included in such combinations.

The individual components of such combinations may be administered either separately, sequentially or simultaneously in separate or combined pharmaceutical formulations.

When the compounds of the invention are used with a second therapeutic and/or prophylactic agent active against the same virus, the dose of each compound may either be the same as or different from that employed when each compound is used alone. Appropriate doses will be readily appreciated by those skilled in the art.

Pharmaceutical formulations include those suitable for oral, rectal, nasal, topical (including buccal and sub-lingual), vaginal or parenteral (including intramuscular, sub-cutaneous and intravenous) administration, or those in a form suitable for administration to the respiratory tract (including the nasal passages) for example by inhalation or insufflation. The formulations may, where appropriate, be conveniently presented in discrete dosage units, and may be prepared by any of the methods well known in the art of pharmacy. These methods include the step of bringing into association the active compound with liquid carriers or finely divided solid carriers or both, and then, if necessary, shaping the product into the desired formulation.

Pharmaceutical formulations suitable for oral administration may conveniently be presented as discrete units such as capsules, cachets or tablets each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may for example be in the form of aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles, which may include edible oils, or preservatives.

The compounds according to the invention may also be formulated for parenteral administration by injection, for example bolus injection, or continuous infusion, and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulating agents such as suspending, stabilising and/or dispersing agents. Alternatively, the active ingredient may be in powder form, obtained by aseptic isolation of sterile solid or by lyophilisation from solution, for constitution with a suitable vehicle, eg. sterile, pyrogen-free water, before use.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base, and will in general also contain one or more emulsifying agents, stabilising agents, dispersing agents, suspending agents, thickening agents, or colouring agents.

Formulations suitable for topical administration in the mouth include lozenges comprising active ingredient in a flavoured base, usually sucrose and gum acacia or gum tragacanth; pastilles comprising the active ingredient in an inert base such as gelatin or sucrose and gum acacia; and mouthwashes comprising the active ingredient in a suitable liquid carrier.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping moulds.

Formulations suitable for vaginal administration may be presented as pessaries, tampons, creams, gels, pastes, foams or sprays containing in addition to the active ingredient such carriers as are known in the art to be appropriate.

For administration to the respiratory tract, including intranasal administration, the neuramimidase inhibitors may be administered by any of the methods and formulations employed in the art for administration to the respiratory tract.

Thus in general the compounds may be administered in the form of a solution or a suspension or as a dry powder.

Solutions and suspensions will generally be aqueous, for example prepared from water alone (for example sterile or pyrogen-free water) or water and a physiologically acceptable co-solvent (for example ethanol, propylene glycol or polyethylene glycols such as PEG 400).

Such solutions or suspensions may additionally contain other excipients for example preservatives (such as benzalkonium chloride), solubilising agents/surfactants such as polysorbates (eg. Tween 80, Span 80, benzalkonium chloride), buffering agents, isotonicity-adjusting agents (for example sodium chloride), absorption enhancers and viscosity enhancers. Suspensions may additionally contain suspending agents (for example microcrystalline cellulose, carboxymethyl cellulose sodium).

Solutions or suspensions are applied directly to the nasal cavity by conventional means, for example with a dropper, pipette or spray. The formulations may be provided in single or multidose form. In the latter case a means of dose metering is desirably provided. In the case of a dropper or pipette this may be achieved by the patient administering an appropriate, predetermined volume of the solution or suspension. In the case of a spray this may be achieved for example by means of a metering atomising spray pump.

Administration to the respiratory tract may also be achieved by means of an aerosol formulation in which the compound is provided in a pressurised pack with a suitable propellant, such as a chlorofluorocarbon (CFC), for example dichlorodifluoromethane, trichlorofluoromethane or dichlorotetrafluoroethane, carbon dioxide or other suitable gas. The aerosol may conveniently also contain a surfactant such as lecithin. The dose of drug may be controlled by provision of a metered valve.

Alternatively the compounds may be provided in the form of a dry powder, for example a powder mix of the compound in a suitable powder base such as lactose, starch, starch derivatives such as hydroxypropylmethyl cellulose and polyvinylpyrrolidine (PVP). Conveniently the powder carrier will form a gel in the nasal cavity. The powder composition may be presented in unit dose form, for example in capsules or cartridges of eg. gelatin, or blister packs from which the powder may be administered by means of an inhaler.

In formulations intended for administration to the respiratory tract, including intranasal formulations, the compound will generally have a small particle size, for example of the order of 5 microns or less. Such a particle size may be obtained by means known in the art, for example by micronisation.

When desired, formulations adapted to give sustained release of the active ingredient may be employed.

Preferably the compounds of the invention are administered to the respiratory tract by inhalation, insufflation or intranasal administration, or a combination thereof.

"Relenza" is administered by oral inhalation as a free-flow powder via a "Diskhaler" (Oseltamivir). A similar formulation would be suitable for the present invention.

Thus, according to an eighth aspect of the present invention there is provided an inhaler which contains a formulation as defined above.

It will be appreciated that the inhaler may also be in the form of a meter dose aerosol inhaler.

For the purposes of this specification it will be clearly understood that the word "comprising" means "including but not limited to", and that the word "comprises" has a corresponding meaning.

All publications, including but not limited to patents and patent applications, cited in this specification are herein incorporated by reference as if each individual publication were specifically and individually indicated to be incorporated by reference herein as though fully set forth.

DETAILED DESCRIPTION OF THE INVENTION

The invention will now be described in detail by way of reference only to the following non-limiting examples.

TABLE 1

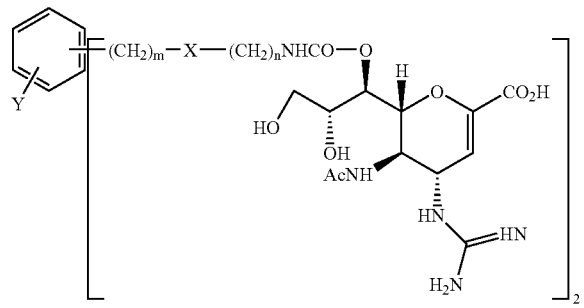

| Compound No | Aryl Substituent1 Y | Aryl substitution | Group m | Group X | Group n |
|---|---|---|---|---|---|
| 1 | H | 1,3 | 0 | CONH | 4 |
| 2 | H | 1,3 | 1 | NHCO | 2 |
| 3 | H | 1,3 | 0 | $SO_2NH$ | 4 |
| 4 | H | 1,4 | 1 | NHCO | 2 |
| 5 | H | 1,4 | 0 | CONH | 3 |
| 6 | H | 1,4 | 0 | CONH | 6 |
| 7 | H | 1,2 | 0 | CONH | 6 |
| 8 | H | 1,3 | 0 | CONH | 6 |
| 9 | 5-$CO_2H$ | 1,3 | 0 | CONH | 3 |
| 10 | 5-$CH_3$ | 1,3 | 0 | NHCONH | 6 |
| 11 | H | 1,3 | 0 | CONH | 3 |
| 12 | H | 1,2 | 0 | CONH | 3 |
| 13 | H | 1,4 | 1 | CONH | 3 |
| 14 | H | 1,2 | 1 | CONH | 3 |

Machine Methods

Green Method (LC/MS)

Micromass Platform II mass spectrometer operating in positive ion electrospray mode, mass range 100–1000 amu.
Column: 3.3 cm×4.6 mm ID, 3 μm ABZ+PLUS
Flow Rate: 3 ml/min
Injection Volume: 5 μl
Solvent A: 95% acetonitrile+0.05% formic acid
Solvent B: 0.1% formic acid+10 mMolar ammonium acetate
Gradient: 0% A/0.7 min, 0–100% A/3.5 min, 100% A/1.1 min, 100–0% A/0.2 min Purple Method (Mass Directed Autoprep HPLC)

The prep column used was a Supelcosil ABZplus (10 cm×2.12 cm)
UV wavelength: 200–320 nM
Flow: 20 ml/min
Injection Volume: 1 ml
Solvent A: 0.1% formic acid
Solvent B: 95% acetonitrile+5% formic acid
Gradient: 100% A/1 min, 100–80% A/9 min, 80–1% A/3.5 min, 1% A/1.4 min, 1–100% A/0.1 min Turquoise Method (Autoprep HPLC)

The prep column used was a Supelcosil ABZplus (10 cm×2.12 cm).
UV wavelength: 230 nm
Flow: 4 ml/min
Injection Volume: 2 ml
Solvent A: acetonitrile+0.05% TFA
Solvent B: water+0.1% TFA Method A (LC/MS)

Micromass Platform II mass spectrometer operating in positive ion electrospray mode, mass range 100–1000 amu.
Column: 3.3 cm×4.6 mm ID, 3 μm ABZ+PLUS
Flow Rate: 3 ml/min
Injection Volume: 5 μl
Solvent A: 95% acetonitrile+0.05% formic acid
Solvent B: 0.1% formic acid+10 mMolar ammonium acetate
Gradient: 0% A/0.7 min, 0–100% A/3.5 min, 100% A/1.1 min, 100–0% A/0.2 min Method B (LC/MS)

Waters ZQ mass spectrometer operating in positive ion electrospray mode, mass range 100–1000 amu.
Column: 3.3 cm×4.6 mm ID, 3 μm ABZ+PLUS
Flow Rate: 3 ml/min
Injection Volume: 5 μl
Solvent A: 95% acetonitrile+0.05% formic acid
Solvent B: 0.1% formic acid+10 mMolar ammonium acetate
Gradient: 0% A/0.7 min, 0–100% A/3.5 min, 100% A/1.1 min, 100–0% A/0.2 min, Method C (Autoprep HPLC)

The prep column used was a Supelcosil ABZplus (10 cm×2.12 cm).
UV wavelength: 230 nm
Flow: 4 ml/min
Injection Volume: 2 ml
Solvent A: acetonitrile+0.05% TFA
Solvent B: water+0.1% TFA
Gradient: 0–40% A/20 min, 40% A/20 min, 40–100% A/0.3 min, 100% A/15 min, 100–0% A/3 min Method D (Mass Directed Autoprep HPLC)

The prep column used was a Supelcosil ABZplus (10 cm×2.12 cm)
UV wavelength: 200–320 nM
Flow: 20 ml/min
Injection Volume: 1 ml
Solvent A: 0.1% formic acid
Solvent B: 95% acetonitrile+5% formic acid
Gradient: 100% A/1 min, 100–80% A/9 min, 80–1% A/3.5 min, 1% A/1.4 min, 1–100% A/0.1 min Abbreviations
EtOAc ethyl acetate
MeOH methanol
HPLC high pressure liquid chromatography
SPE solid phase extraction
LC/MS Liquid chromatography/mass spectroscopy
DMF N,N-Dimethylformamide
WSCDI 1-(3-Dimethylaminopropyl)-3-ethylcarbodiimide methiodide
HOBt 1-hydroxybenzotriazole
DIPEA N,N-diisopropylethylamine
MeCN acetonitrile
RT room temperature
EtOAc ethyl acetate
$MgSO_4$ magnesium sulphate
DMF dimethylformamide

EXAMPLE 1

Preparation of Compound 1

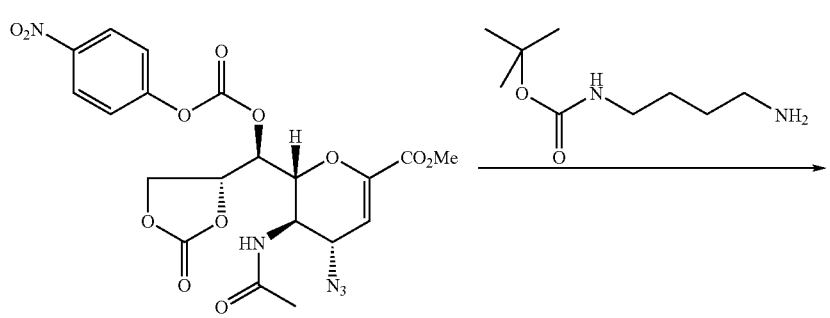

Intermediate 1

-continued

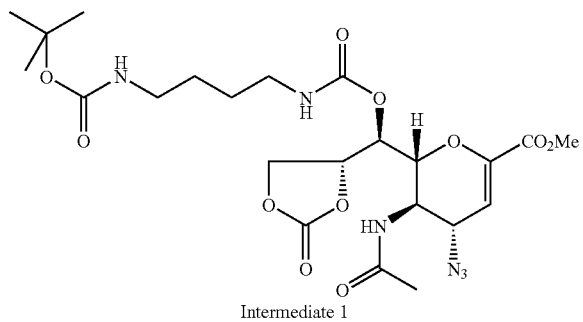

Intermediate 1

(4S, 5R, 6R)-5-Acetylamino-4-azido-6-[(S)-4-nitrophenoxycarbonyloxy)-(2-oxo-[1,3]dioxolan-4R-yl)methyl]-5,6-dihydro-4H-pyran-2-carboxylic acid methylester (see *Eur. J. Med. Chem.* 1999, 34, 563–574) (2.00 g, 3.8 mmol) was dried by azeotroping 3 times from anhydrous toluene then dissolved in anhydrous acetonitrile (20 ml) with the addition of a few 3 angstrom molecular sieve pellets. The stirred solution was treated with N-tert-butoxycarbonyl 1,4-diaminobutane (0.72 g, 3.8 mmol) and triethylamine (0.43 g, 4.2 mmol). The mixture was stirred for 16 h under a nitrogen atmosphere. Volatiles were removed in vacuo to afford a yellow residue. This was redissolved in EtOAc (50 ml), washed with 0.5MHCl (30 ml) then brine (30 ml). The solution was dried ($Na_2SO_4$) and solvent evaporated in vacuo to afford a cream coloured foam. Further purification was by Biotage flash chromatography, eluant initially EtOAc:Cyclohexane (1:1) then EtOAc. Evaporation of solvent in vacuo gave Intermediate 1 (1.26 g, 58% yield) as a white solid. LC/MS (Method B) showed $MH^+=571$; $T_{RET}=2.87$ min

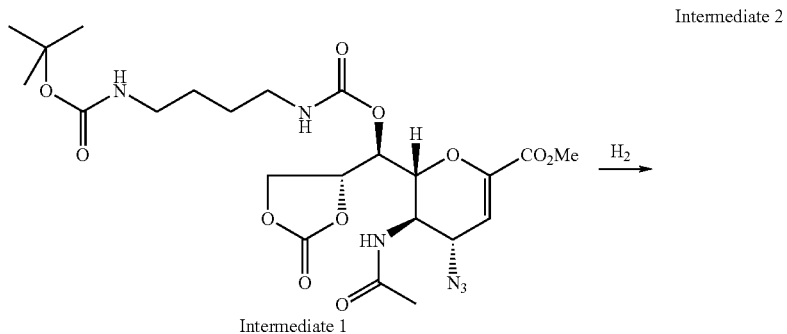

Intermediate 2

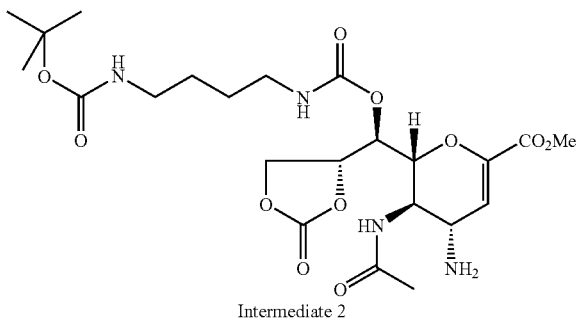

Intermediate 2

Intermediate 1 (0.76 g, 1.33 mmol) was dissolved in ethanol (24 ml) and subjected to catalytic hydrogenation over Lindlar Catalyst (0.095 g) for 16 h. Catalyst was removed by filtration and evaporation of solvent in vacuo gave Intermediate 2 (0.72 g, 99% yield) as a cream coloured foam. LC/MS (Method A) showed $MH^+=545$; $T_{RET}=2.24$ min

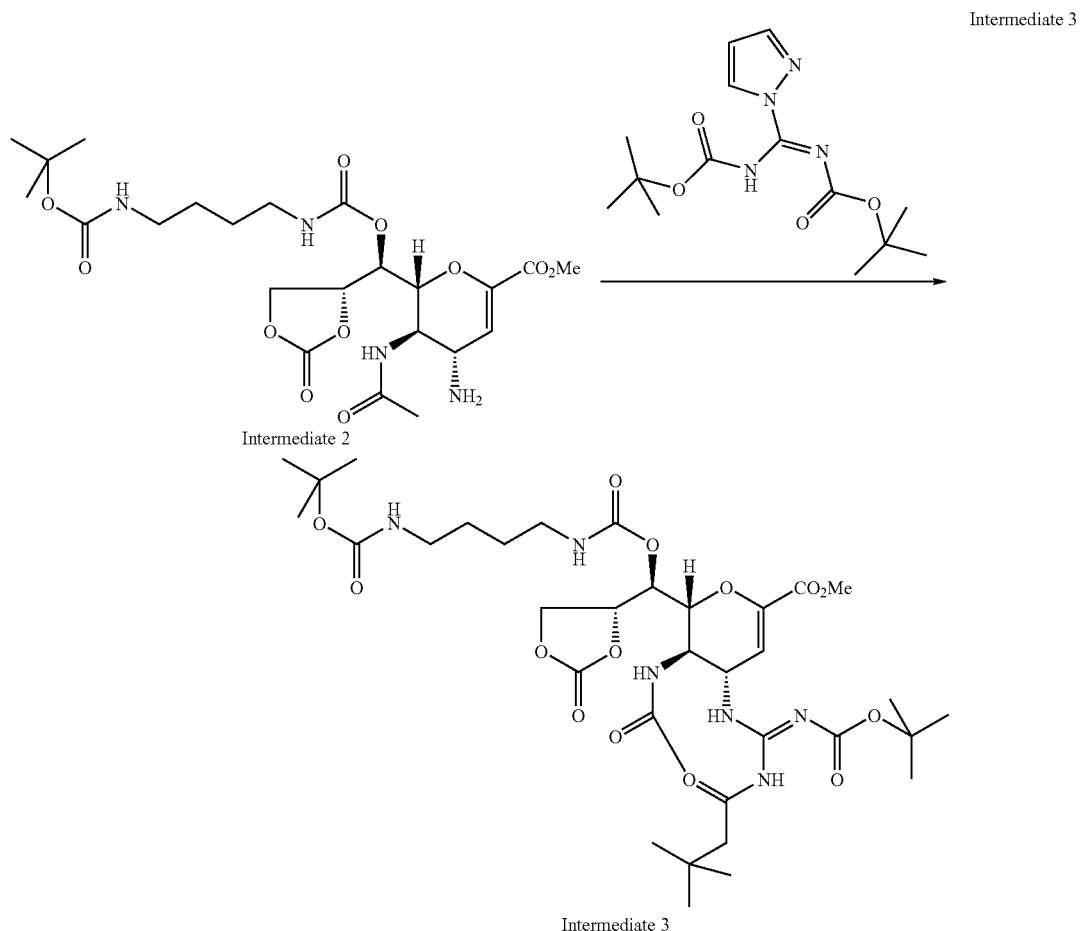

Intermediate 2 (0.72 g, 1.32 mmol) was dissolved in tetrahydrofuran (7 ml) and treated with N,N'-bis-(tert-butoxycarbonyl)-1-guanylpyrazole (0.45 g, 1.45 mmol). The mixture was stirred under a nitrogen atmosphere for 16 h. Volatiles were removed in vacuo to give a solid residue which was purified by Biotage flash chromatography; eluant initially EtOAc:Cyclohexane (1:1) then EtOAc:Cyclohexane (5:3). Evaporation of solvent in vacuo afforded Intermediate 3 (0.48 g, 46% yield) as a white solid. LC/MS (Method A) showed MH$^+$=787; T$_{RET}$=3.64 min

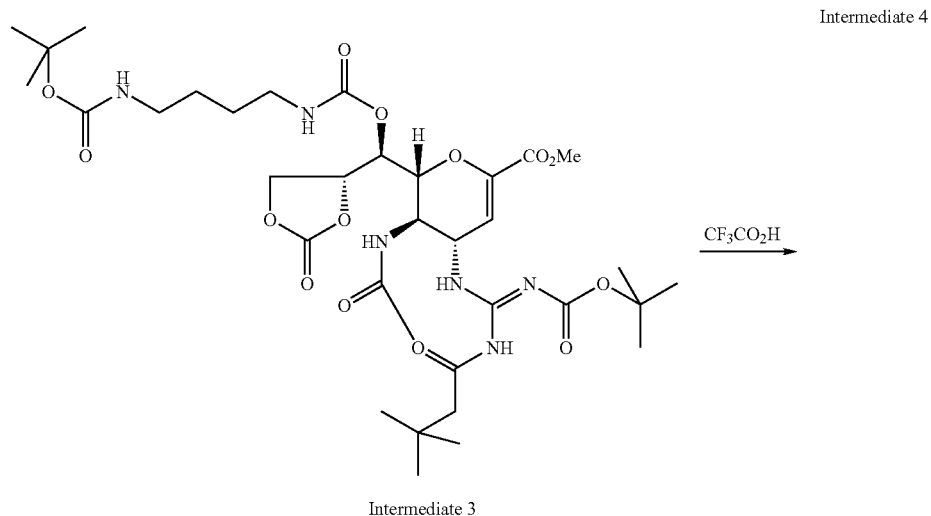

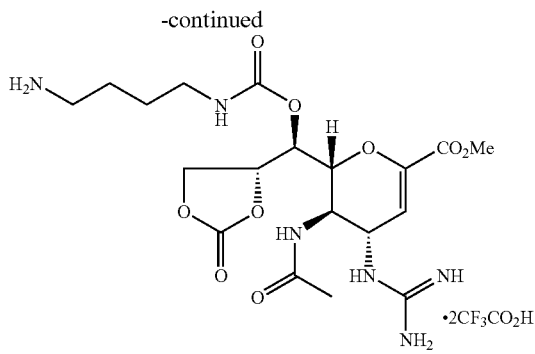

Intermediate 4

Intermediate 3 (0.48 g, 0.61 mmol) was dissolved in dichloromethane (19 ml). The solution was cooled in an ice bath and trifluoroacetic acid (19 ml) was added portionwise over 5 minutes. The mixture was then stirred for 1 h under a nitrogen atmosphere before being allowed to warm to ambient temperature and stirred a further 16 h. Volatiles were removed in vacuo, and the residue azeotroped from toluene to remove remaining trifluoroacetic acid. Trituration with diethyl ether (20 ml) afforded a white solid which was separated to give Intermediate 4 (0.50 g). LC/MS (Method B) showed (M−H)⁻=485; $T_{RET}$=0.52 min.

Intermediate 4 (0.050 g, 0.07 mmol) was dried by azeotroping 3 times from anhydrous toluene and then dissolved in a mixture of anhydrous acetonitrile (2 ml) and anhydrous DMF (1 ml). The solution was treated successively with isophthalic acid (0.005 g, 0.03 mmol), HOBt (0.010 g, 0.07 mmol), WSCDI (0.013 g, 0.07 mmol) and DIPEA (0.026 g, 0.20 mmol). The mixture was stirred for 16 h under a nitrogen atmosphere. Volatiles were removed in vacuo to afford a yellow residue which was purified by mass-directed preparative HPLC (method D) to give Intermediate 5 (0.013 g) as a white solid. LC/MS (Method A) showed (M+2H⁺)/2=552; $T_{RET}$=2.05 min

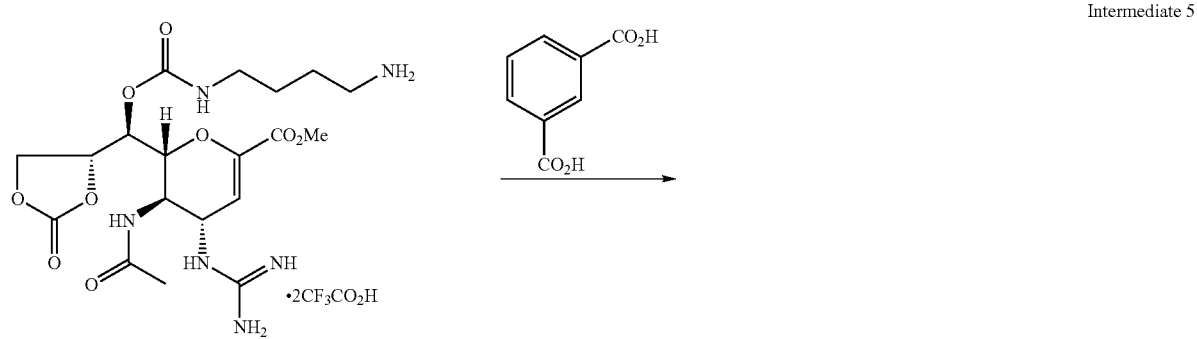

Intermediate 4

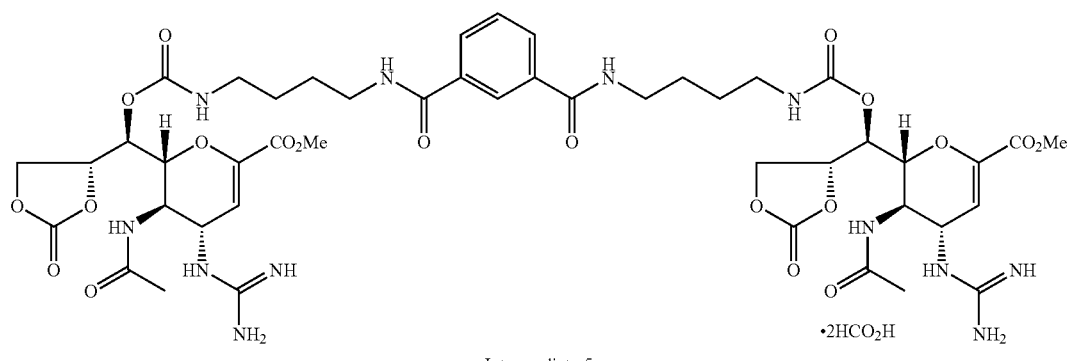

Intermediate 5

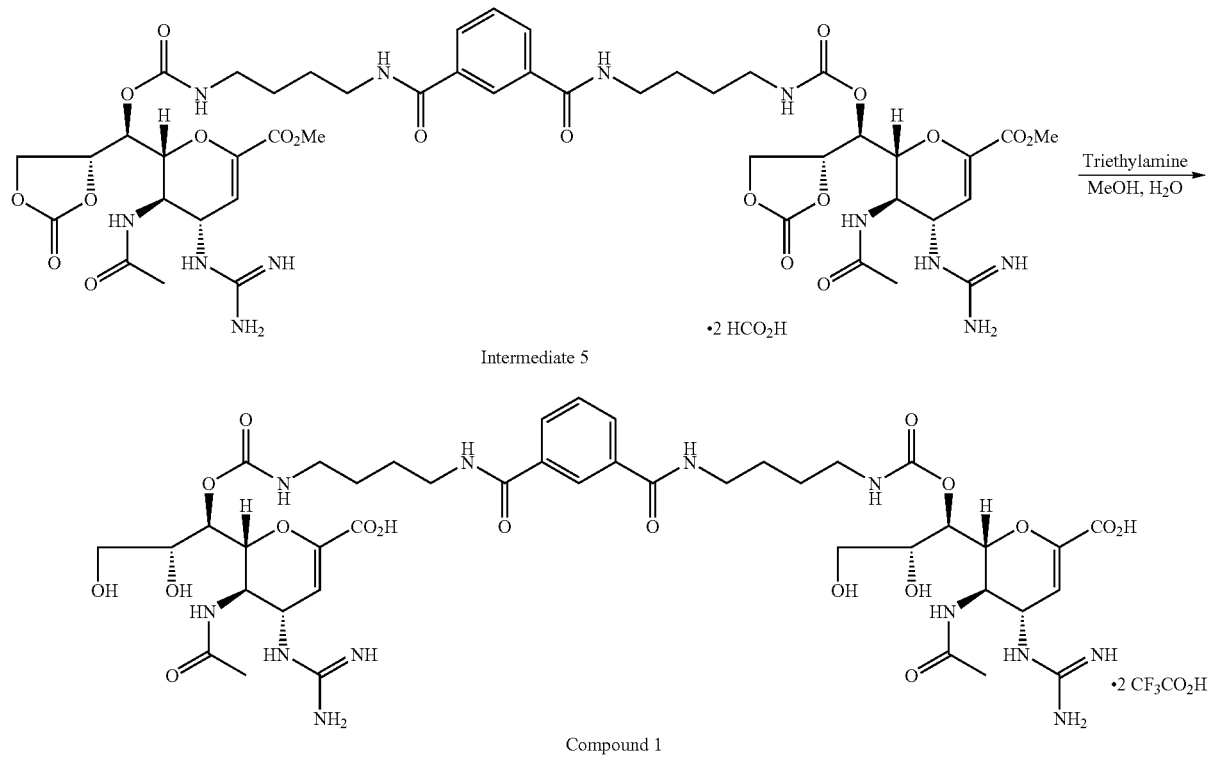

Compound 1

Intermediate 5

Compound 1

Intermediate 5 (0.012 g, 0.01 mmol) was dissolved in a mixture of water (0.5 ml) and methanol (0.5 ml). The resulting solution was treated with triethylamine (0.090 g, an excess). The mixture was stirred for 50 min before rapid removal of volatiles in vacuo to give a white solid residue. Purification by preparative HPLC (method C) gave Compound 1 (0.002 g) as a white solid. LC/MS (Method B) showed $(M+2H^+)/2=512$; $T_{RET}=1.77$ min

EXAMPLE 2

Preparation of Compound 2

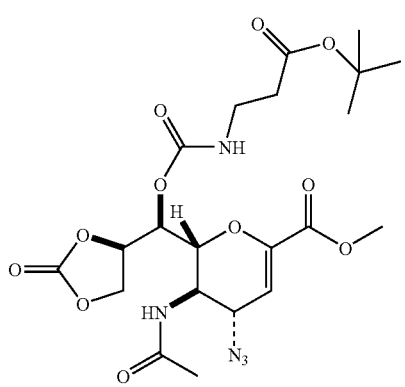

Intermediate 6

(4S, 5R, 6R)-5-Acetylamino-4-azido-6-[(S)-4-[(S)-4-nitrophenoxycarbonyloxy)-(2-oxo-[1,3]dioxolan-4R-yl)methyl]-5,6-dihydro-4H-pyran-2-carboxylic acid methylester (see Eur. J. Med. Chem. 1999, 34, 563–574) (4.0 g) was azeotroped with toluene (50 mL) and dissolved in MeCN (40 mL) and triethylamine (1.12 mL) and 3-aminopropionic acid t-butyl ester hydrochloride (1.396 g) added. After 3 days at RT, the solvent was removed and the residue diluted with EtOAc (150 mL). This was washed with 5% citric acid solution (2×50 mL), dried (MgSO$_4$) and concentrated. Purification by Biotage eluting with 1:1 cyclohexane:EtOAc, then 60:40 then 65:35 cyclohexane:EtOAc gave Intermediate 6 as a colourless foam (3.45 g).

$^1$H-NMR (400 MHz, CDCl$_3$) δ 6.72 (d, 1H), 5.97 (d, 1H), 5.53 (t, 1H), 5.40 (t, 1H), 5.03–4.95 (m, 2H), 4.92 (dd, 1H), 4.74–4.64 (m, 2H), 3.83 (s, 3H), 3.64–3.54 (m, 1H), 3.38–3.27 (m, 2H), 2.65–2.56 (m, 1H), 2.52–2.43 (m, 1H), 2.06 (s, 3H), 1.70 (s, 1H), 1.48 (s, 9H).

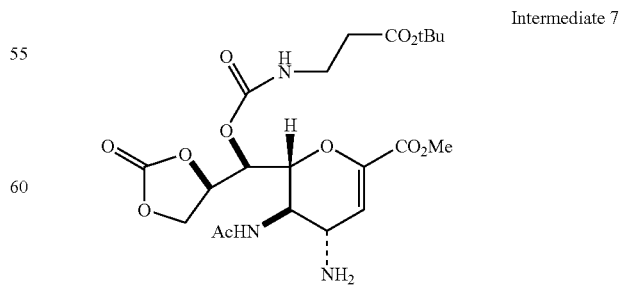

Intermediate 7

Similarly prepared to Intermediate 2 from Intermediate 6. LC/MS (green method) MH$^+$ 504, $T_{RET}=2.22$ min

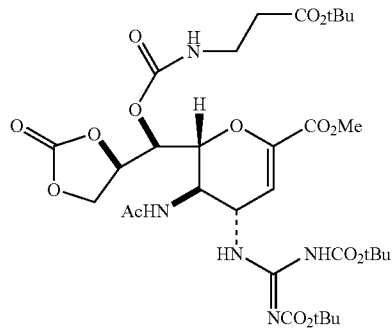

Intermediate 8

Intermediate 8 was prepared similarly to Intermediate 3 from Intermediate 7
LC/MS (green method) MH+ 744, $T_{RET}$=3.66 min

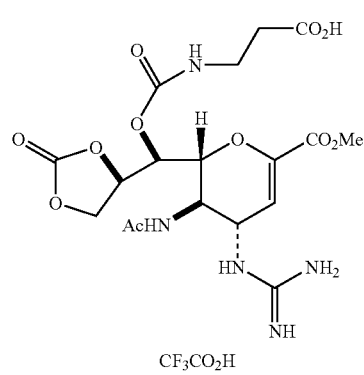

Intermediate 9

Intermdiate 8 (1.44 g), trifluoroacetic acid (20 mL), dichloromethane (20 mL) and anisole (2 mL) were stirred at RT for 3 h after which the volatiles were removed in vacuo. The residue was triturated with Et$_2$O (2×25 mL) and then dried in vacuo to afford Intermediate 9 as a white solid (1.22 g).
LC/MS (green method) MH+ 488, $T_{RET}$=1.25 min Intermediate 9 (0.12 g), DIPEA (0.14 mL), m-xylylenediamine (0.0132 mL) and benzotriazole-1-yloxytrispyrrolidinophosphonium hexafluorophosphate (0.104 g) were mixed at RT for 2 days and then concentrated in vacuo. Purification using mass directed HPLC (purple method) gave Intermediate 10 (0.038 g).

LC/MS (green method) MH+/2 538, $T_{RET}$=1.74 min

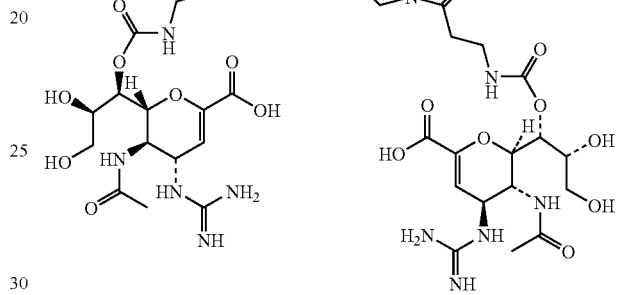

Compound 2

Intermediate 10 (0.038 g), water (1.5 mL), methanol (1.5 mL) and triethylamine (0.5 mL) were mixed at RT for 1 h. The volatiles were removed in vacuo and the aqueous residue acidified to pH4 with trifluoroacetic acid. Reverse phase HPLC (turquoise method) eluting with 0–17.5% MeCN over 30 min afforded Compound 2 (7.6 mg).

LC/MS (green method) MH+/2 497, $T_{RET}$=1.64 min

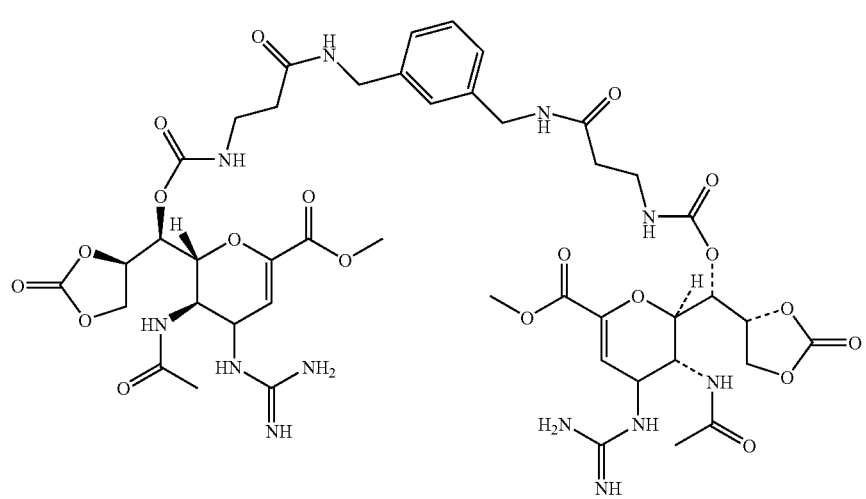

Intermediate 10

EXAMPLE 3

Preparation of Compound 3

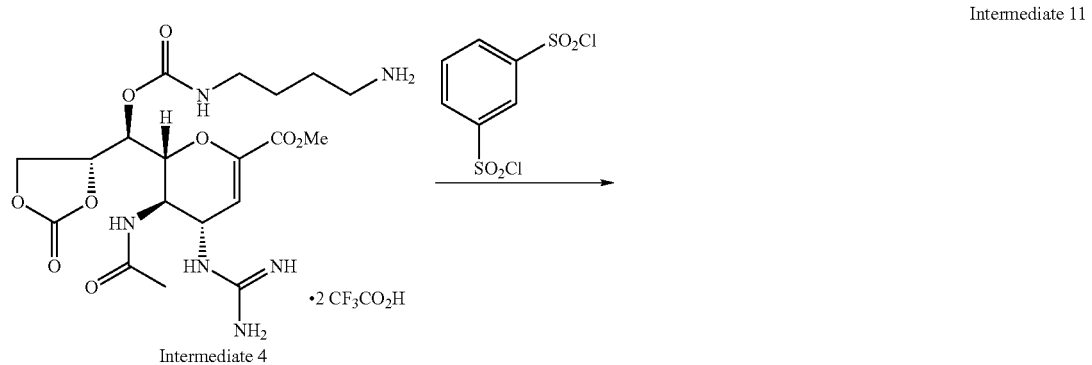

Intermediate 4

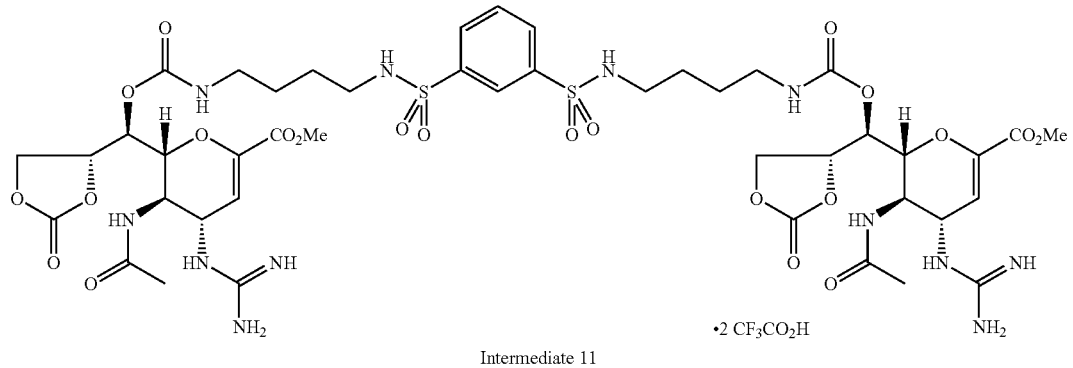

Intermediate 11

Intermediate 4 (0.075 g, 0.11 mmol) was dried by azeotroping 3 times from anhydrous toluene. The dried solid was dissolved in a mixture of anhydrous chloroform (2 ml) and anhydrous DMF (1 ml) with addition of DIPEA (0.056 g, 0.43 mmol). The resulting clear solution was added to 1,3-Benzenedisulphonyl chloride (0.014 g, 0.05 mmol) and the mixture stirred for 1 h under a nitrogen atmosphere. Volatiles were removed in vacuo to give a residue which was further purified by reverse phase SPE (eluant 15% aqueous acetonitrile) to afford Intermediate 11 (0.020 g) as a white solid. LC/MS (Method B) showed $(M+2H^+)/2=588$; $T_{RET}=2.09$ min

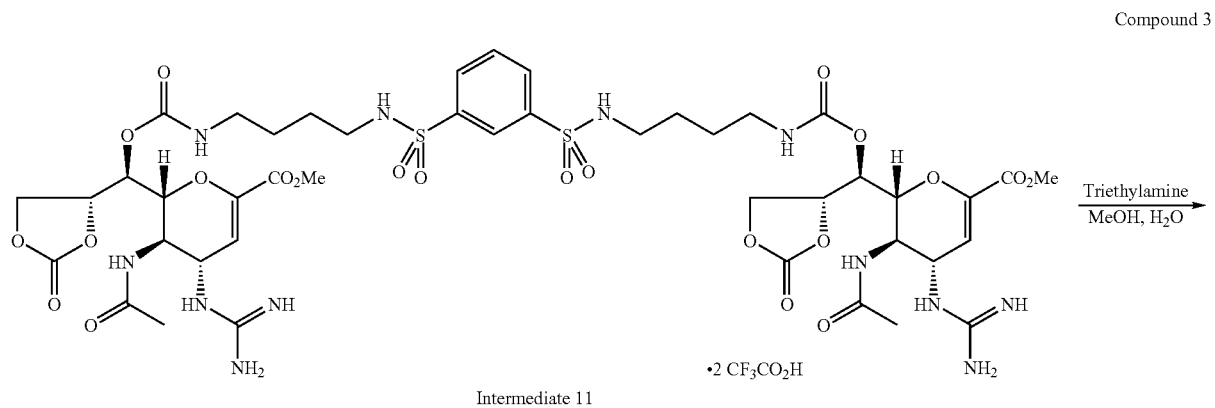

Intermediate 11

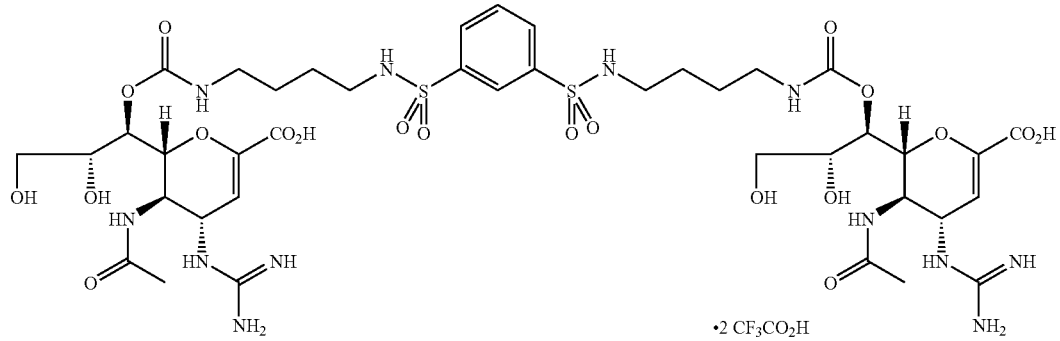

Example 3

Intermediate 11 (0.020 g, 0.014 mmol) was dissolved in a mixture of water (0.5 ml) and methanol (0.5 ml). The resulting solution was treated with triethylamine (0.090 g, an excess). The mixture was stirred for 50 min before rapid removal of volatiles in vacuo to give a white solid residue. Purification by preparative HPLC (method C) gave Compound 3 (0.006 g) as a white solid. LC/MS (Method A) showed $(M+2H^+)/2=548$; $T_{RET}=1.99$ min.

EXAMPLE 4

Preparation of Compound 4

Similarly prepared to Intermediate 10 from Intermediate 9 and p-xylylenediamine to afford Intermediate 12 (0.038 g). LC/MS (green method) $MH^+/2$ 538, $T_{RET}=1.94$ min Compound 4

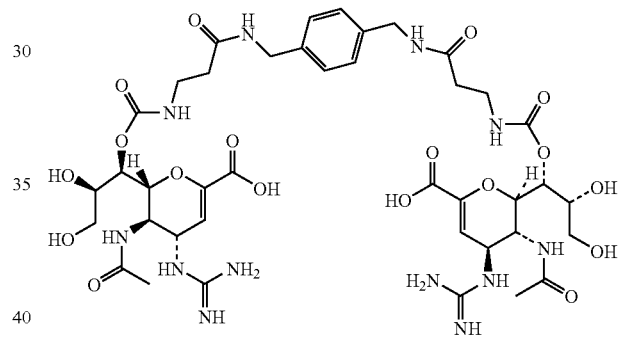

Compound 4 was similarly prepared to Compound 2 from Intermediate 12.
LC/MS (green method) $MH^+/2$ 497, $T_{RET}=1.62$ min Intermediate 12

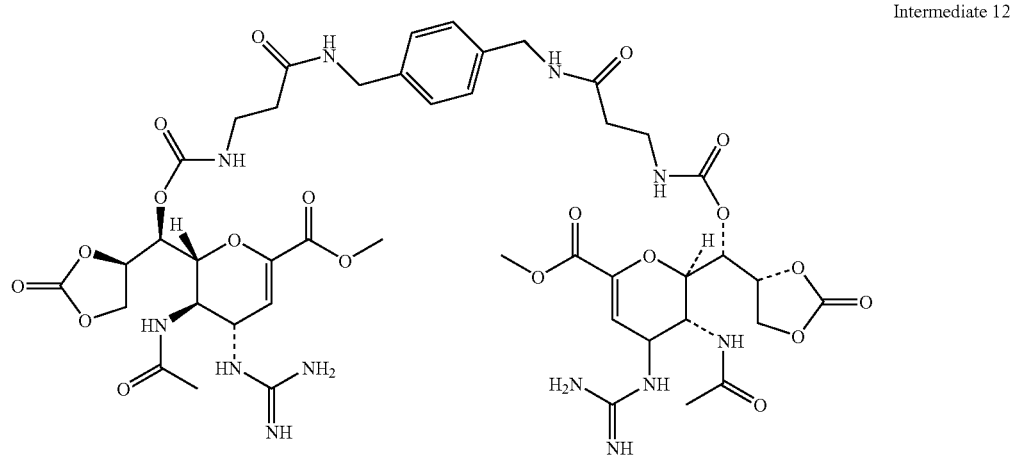

EXAMPLE 5

Preparation of Compound 5 by Reaction of Intermediate 13 and Terephthalic Acid

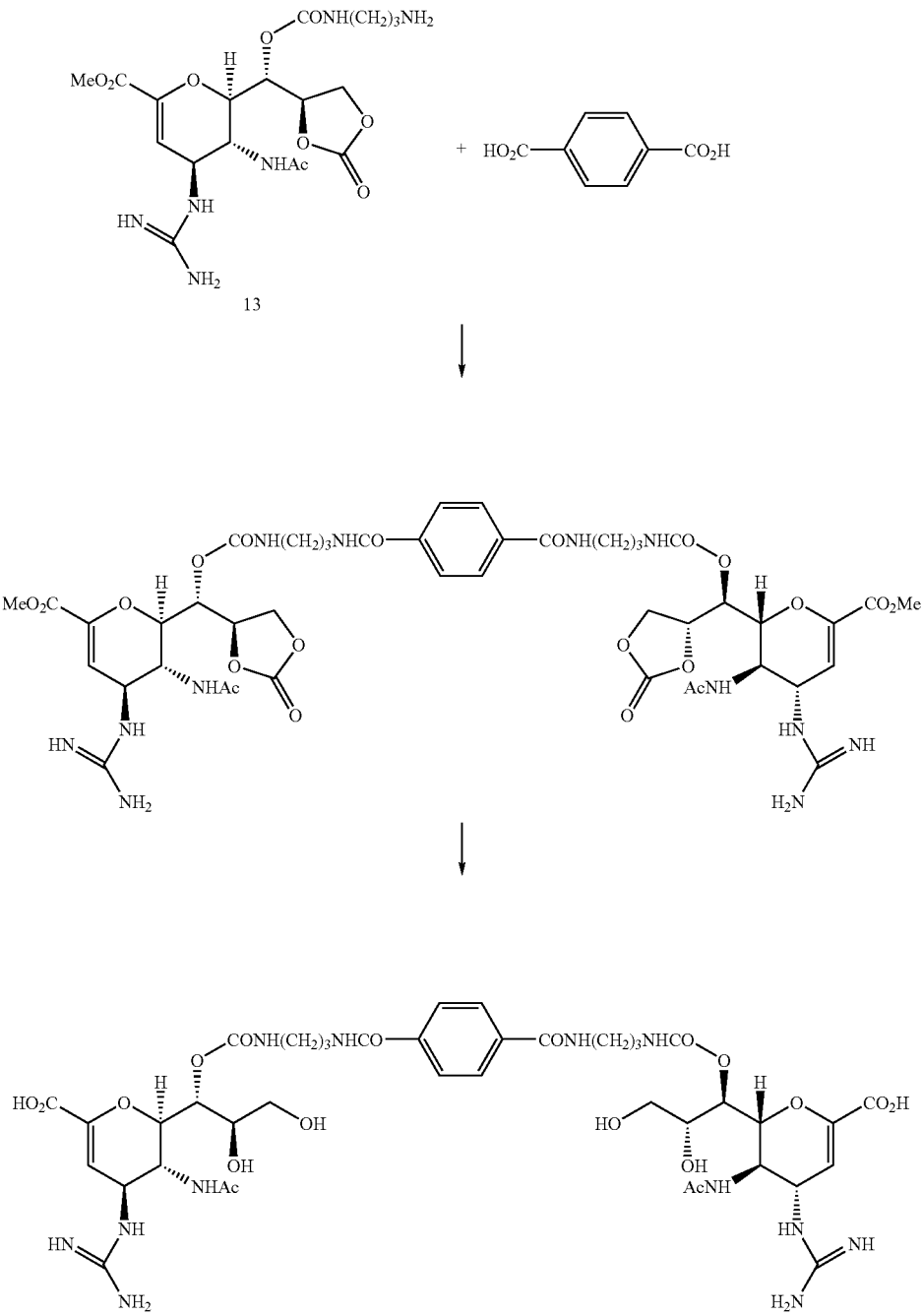

The aminopropyl Intermediate 13 was prepared following a similar sequence of steps to that described for the analogous aminobutyl Intermediate 4 in Example 1.

Terephthalic acid (5.93 mg, 0.0357 mmole), Intermediate 13 (50 mg, 0.071 mmole) and benzotriazol-1-yloxy-tris(dimethylamino)phosphonium hexafluorophosphate (BOP) (37.7 mg, 0.0852 mmole) were dissolved in DMF (2 ml) to which was added di-isopropylethylamine (DIPEA, 91.8 mg, 0.71 mmole). The resulting mixture was stirred at room temperature for 5 hours. The reaction mixture was purified by reverse phase HPLC using a Waters Symmetry C18 column (5 micron 19×100 mm), and gradient elution as shown in the following Table, to afford the protected dimer (19.5 mg, 51%), MS 1075 (M+H)$^+$

| Time (minutes) | A % | B % | Flow rate (ml/min) |
|---|---|---|---|
| 0 | 100 | 0 | 6 |
| 2 | 100 | 0 | 6 |
| 22 | 40 | 60 | 6 |
| 32 | 40 | 60 | 6 |
| 35 | 100 | 0 | 6 |
| 42 | 100 | 0 | 6 |

A = Water containing 0.1% trifluoroacetic acid
B = Acetonitrile containing 0.06% trifluoroacetic acid The protected dimeric compound (19.5 mg, 0.0182 mmole) was dissolved in a mixture of water/methanol/triethylamine in the ratio 4:4:1 (2 ml) and stirred at room temperature for 1 hour then evaporated to dryness under reduced pressure. Remaining triethylamine was removed by repeated addition of water and evaporation under reduced pressure. The remaining residue was purifed by reverse phase HPLC using a Waters Symmetry C18 column (5 micron, 19×100 mm), and gradient elution as shown in the following Table, to afford the dimer 5 as a white solid (10.8 mg, 60%) after freeze-drying.

| Time (minutes) | A % | B % | Flow rate (ml/min) |
|---|---|---|---|
| 0 | 100 | 0 | 6 |
| 2 | 100 | 0 | 6 |
| 22 | 60 | 40 | 6 |
| 32 | 60 | 40 | 6 |
| 35 | 100 | 0 | 6 |
| 42 | 100 | 0 | 6 |

A = Water containing 0.1% trifluoroacetic acid
B = Acetonitrile containing 0.06% trifluoroacetic acid

MS 498.3 $(M+2H)^{2+}$, 995.2 $(M+H)^+$ $^1$H-nmr ($D_2O$) δ (ppm): 1.79 (t, 4H); 1.90 (s, 6H); 3.14 (t, 4H); 3.42 (m, 6H); 3.62 (dd, 2H); 3.98 (m, 2H); 4.08 (dd, 2H); 4.37 (dd, 2H); 4.52 (dd, 2H); 4.88 (dd, 0.2H); 5.92 (d, 2H); 7.79 (s, 4H).

EXAMPLE 6

Preparation of Compound 5 by Reaction of Intermediates 14 and 15

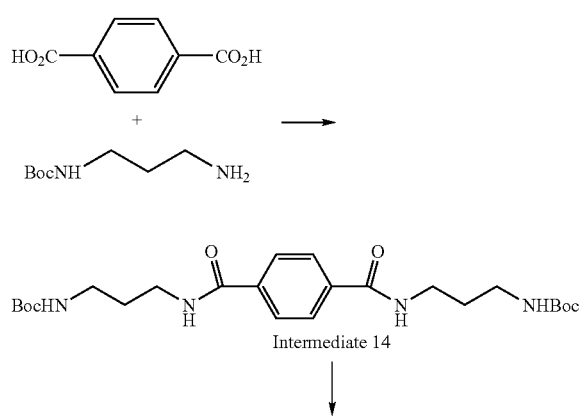

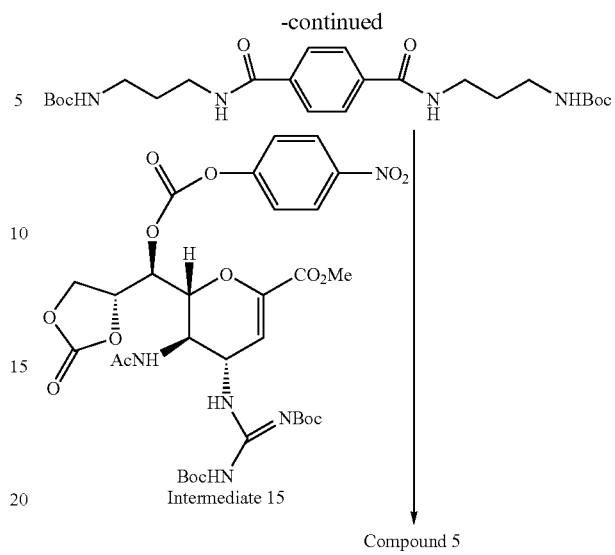

Intermediate 14

To a suspension of terephthalic acid (141.9 mg, 0.85 mmole) and N-Boc-1,3-diaminopropane (300 mg, 1.72 mmole) in DMF (12 ml) was added triethylamine (392 mg, 3.88 mmole) with stirring at room temperature. To the white suspension was added in portions BOP (771 mg, 1.74 mmole). After addition of the first portion of BOP (about 300 mg) the reaction mixture became a clear solution. The reaction mixture was stirred at room temperature for 16 hours and then evaporated in vacuo to remove DMF. The residue was stirred in water (10 ml) at room temperature for 3 hours and then the solid collected by filtration. The solid was washed with water (4×5 ml) and filtered. The filter cake was dissolved in hot methanol (4 ml) and then diluted with water (9 ml). The suspension was stirred at room temperature for 3 hours and then filtered. The solid was washed with water (4×5 ml), then dissolved in boiling methanol (4 ml) and cooled to room temperature. The crystalline suspension was allowed to agitate at room temperature overnight. The solid was filtered off, washed with cold methanol and air-dried to give the bis-amido product as a white solid (365 mg, 89.7%), MS 479 $(M+H)^+$ The Boc-protected bis-amide (360 mg) was stirred in a mixture of trifluoroacetic acid (TFA) (2 ml) and dichloromethane (2 ml) at room temperature for 4 hr, then evaporated to dryness under vacuum. The residue was dissolved in water (6 ml) and freeze-dried to remove any excess TFA and afford the Intermediate 14 (TFA salt) as a white solid (379 mg, 98%), MS 279 (Base +H)+

Intermediate 15

A solution of methyl (2R, 3R, 4 S)-3-(acetylamino)-4-({[(tert-butoxycarbonyl)amino][(tert-butoxycarbonyl)imino]methyl}amino)-2-{(S)-hydroxy[(4R)-2-oxo-1,3-dioxolan-4-yl]methyl}-3,4-dihydro-2H-pyran-6-carboxylate (113 mg, 0.197 mmol) in dry pyridine (3 ml) containing 4-dimethylaminopyridine (120 mg, 0.982 mmol) was treated with 4-nitrophenylchloroformate (199 mg, 0.987 mmol) at 22° C. The mixture was stirred at 22° C. for 17 h, then the pyridine removed in vacuo. The residue was purified by SPE chromatography (5 g cartridge) eluting with cyclohexane-ethyl acetate (4:1–2:1) to afford Intermediate 15 as a pale yellow gum (96 mg, 66%).

NMR δ($CDCl_3$) 11.3 (1Hs, NH), 8.58 (1H brd, NH), 8.26 (2H, AA'BB', aromatic CH's), 7.56 (2H, AA'BB', aromatic CH's), 6.82 (1H brd, NH), 5.93 (1Hd, =CH), 5.54 (1Hdd, CH), 5.20 (1Hdt, CH), 5.10 (1Hdt, Ch), 4.78 (2Hm, 2×CH), 4.44 (1H brq, CH), 4.28 (1Hdd, CH), 3.82 (3Hs CH3), 1.91 (3Hs, CH3), and 1.48 (18Hs, 2× tert butyl).

LCMS $R_t$=3.87 min. (MH$^+$=738, MH$^-$=736)

Compound 5

Intermediate 14 (38.9 mg, 0.0768 mmole) and Intermediate 15 (2 equivalents) were dissolved in pyridine (0.5 ml) and the resulting mixture was stirred at room temperature for 16 hr and then evaporated to dryness under vacuum. The residue was partitioned between dichloromethane (15 ml) and water (3 ml). The organic layer was washed with water (2×2 ml), then evaporated to dryness to give a gummy residue which was chromatographed on silica gel (20 g, solvent ethyl acetate/methanol 10/1). The protected form of Compound 5 was thus isolated as a white foam (56 mg, 49%).

The protected compound (50 mg, 0.0339 mmole) was treated with TFA and then aqueous triethylamine as described in Example 5 to give Compound 5 (16.8 mg, 50%), MS 995 (M+H)$^+$.

EXAMPLE 7

Compounds 6 to 14 (Table 1) of the invention were prepared in an analogous manner to the Examples given above and the NMR and/or mass spectral data is given below.

Compound 6

MS 540.6 (M+2H)$^{2+}$ $^1$H-nmr (D$_2$O) δ (ppm); 1.43 (br, 8H); 1.51 (br, 4H); 1.65 (br, 4H); 2.00 (s, 6H); 3.12 (m, 4H); 3.41 (m, 4H); 3.43 (dd, 2H); 3.70 (dd, 2H); 4.07 (dd, 2H); 4.18 (dd, 2H); 4.46 (dd, 2H); 4.58 (dd, 2H); 4.98 (dd, 2H); 5.98 (d, 2H); 7.85 (s, 4H).

Compound 7

MS 1079 (M+2H)$^{2+}$, 540.6 (M+2H)$^{2+}$, 360.5 (M+3H)$^{3+}$

Compound 8

MS 1079.5 (M+2H)$^{2+}$, 540.25 (M+2H)$^{2+}$, 360.5 (M+3H)$^{3+}$ $^1$H-nmr (CD$_3$OD) δ (ppm): 1.35 (br, 8H); 1.45 (br, 4H); 1.55 (br, 4H); 1.90 (s, 6H); 3.03 (m, 4H); 3.35 (m, 4H); 3.44 (dd, 2H); 3.56 (dd, 2H); 3.95 (m, 2H); 4.15 (dd, 2H); 4.35 (dd, 2H); 4.52 (dd, 2H); 4.90 (dd, 2H); 5.82 (d, 2H); 7.48 (t, 1H); 7.88 (d, 2H); 8.19 (s, 1H).

Compound 9

MS 1039.1 (M+H)$^+$, 520.3 (M+2H)$^{2+}$ $^1$H-nmr (D$_2$O) δ (ppm): 1.79 (t, 4H); 1.90 (s, 6H); 3.19 (t, 4H); 3.46 (m, 6H); 3.60 (dd, 2H); 4.00 (m, 2H); 4.08 (dd, 2H); 4.37 (dd, 2H); 4.47 (dd, 2H); 4.88 (dd, 2H); 5.88 (d, 2H); 8.28 (s, 1H); 8.49 (s, 2H).

Compound 10

MS 1123.7 (M+H)$^+$, 562.3 (M+2H)$^{2+}$ $^1$H-nmr (CD$_3$OD) δ (ppm): 1.40 (br, 8H); 1.51 (br, 8H); 1.93 (s, 6H); 2.19 (s, 3H); 3.08 (br, 4H); 3.19 (br, 4H); 3.52 (dd, 2H); 3.65 (dd, 2H); 4.01 (m, 2H); 4.16 (dd, 2H); 4.35 (dd, 2H); 4.53 (dd, 2H); 4.98 (dd, 2H); 5.89 (d, 2H); 7.10 (dd, 2H); 7.40 (s, 1H).

Compound 11

MS 995.1 (M+H)$^+$, 498.3 (M+2H)$^{2+}$ $^1$H-nmr (D$_2$O) δ (ppm): 1.75 (t, 4H); 1.90 (s, 6H); 3.15 (t, 4H); 3.45 (m, 6H); 3.60 (dd, 2H); 3.98 (m, 2H); 4.05 (dd, 2H); 4.35 (dd, 2H); 4.45 (dd, 2H); 4.92 (dd, 2H); 5.91 (d, 2H); 7.50 (t, 1H); 7.92 (d, 2H); 8.07 (s, 1H).

Compound 12

MS 995.3 (M+H)$^+$, 498.3 (M+2H)$^{2+}$ $^1$H-nmr (D$_2$O) δ (ppm): 1.78 (t, 4H); 1.92 (s, 6H); 3.15 (t, 4H); 3.40 (t, 4H); 3.46 (dd, 2H); 3.60 (dd, 2H); 3.95 (m, 2H); 4.00 (dd, 2H); 4.35 (dd, 2H); 4.50 (dd, 2H); 4.93 (dd, 2H); 5.83 (d, 2H); 7.62 (dd, 4H).

Compound 13

MS 1023.1 (M+H)$^+$, 512.3 (M+2H)$^{2+}$ $^1$H-nmr (D$_2$O) δ (ppm): 1.65 (t, 4H); 1.85 (s, 6H); 3.02 (t, 4H); 3.15 (t, 4H); 3.42 (dd, 6H); 3.52 (s, 4H); 3.59 (dd, 2H); 3.98 (m, 2H); 4.12 (dd, 2H); 4.40 (dd, 2H); 4.50 (dd, 2H); 4.90 (dd, 2H); 5.90 (d, 2H); 7.30 (s, 4H).

Compound 14

MS 1023.3 (M+H)$^+$, 512.4 (M+2H)$^{2+}$ $^1$H-nmr (D$_2$O) δ (ppm): 1.61 (t, 4H); 1.91 (B, 6H); 3.00 (t, 4H); 3.13 (t, 4H); 3.40 (dd, 6H); 3.57 (s, 4H); 3.58 (dd, 2H); 3.99 (m, 2H); 4.10 (dd, 2H); 4.40 (dd, 2H); 4.50 (dd, 2H); 4.90 (dd, 2H); 5.88 (d, 2H); 7.32 (m, 4H).

EXAMPLE 8

Large Scale Preparation and Purification of Compound 5

TFA Salt to HCl Salt

The 2TFA salt (log) of Compound 5 prepared by Example 6 was dissolved in MeOH/water (1:1 v/v) (150 ml) and applied to a prewashed Amberlite IRA-410 (chloride form) ion exchange column (4×50 cm). The 2HCl salt of Compound 5 was eluted from this column with MeOH/water (1:1 v/v). Fractions containing the 2HCl salt were concentrated in vacuo to give a white foam.

Deprotection

The 2HCl salt (10.4 g) was dissolved in methanol (144 ml) and water (144 ml) and cooled in ice. Triethylamine (7.75 ml) was added in three portions over 10 minutes. The reaction was monitored by reverse phase HPLC. When the reaction was complete, the reaction mixture was evaporated to dryness in vacuo.

A solution of impure Compound 5 containing triethylamine was evaporated to dryness to yield a solid (10.5 g). This solid was dissolved in 80 ml of water and 5 ml of orthophosphoric acid was added to ensure the sample solution was pH 2. This solution (ca 100 ml) was subjected to preparative HPLC using a 7 micron Kromasil C8 column (25 cm×5 cm id.). Chromatographic resolution of Compound 5 was achieved using ion-pair gradient elution where the start mobile phase A was H$_2$O to which had been added 8 g/liter of sodium lauryl sulphate (SLS) and 2 ml/liter H$_3$PO$_4$. The final mobile phase B was 60% CH$_3$CN/H$_2$O to which had been added 8 g/liter SLS and 2 ml/liter H$_3$PO$_4$. Gradient time was 0 to 100% B in 70 minutes holding at 100% B for 20 minutes. Flow was set at 80 ml/min. A total of 4 injections at 25 ml each were done. The detector was set at 260 nm. The fractions, 50 ml each, were bulked according to their analytical purity as measured by HPLC, the specification being >97.5%. This bulked volume was approximately 1800 ml for 4 chromatographic separations. To remove the majority of the phosphate and the lauryl sulphate ions, the aqueous bulk was added to 1200 ml of IRA 410 ion exchange resin in the chloride form and the solution stirred for 1 hour. The resin was removed by filtration and washed with 400 ml of H$_2$O which was combined with the filtrate. The aqueous phase was then passed through a column of IRA 410 in the chloride form (15 cm×2.5 cm id.) to remove any remaining phosphate or lauryl sulphate ion contamination. The column was then washed with 50 ml H$_2$O and combined with the filtrate. After removal of the CH$_3$CN by rotary evaporation at 40° C., the pH was adjusted to 7.0. The aqueous phase was split into 2 portions. The first portion was passed through a column of Amberchrom CG 161 (25 cm×2.5 cm) in order to adsorb Compound 5. This column is a polystyrene divinyl benzene resin which acts as a reversed phase packing material. The column was washed with 300 ml of H$_2$O until the wash was clear of chloride ion, this being checked by the absence of a reaction with AgNO$_3$ solution. The column was eluted with 30% CH$_3$CN/H$_2$O (500 ml). This process was repeated with the second portion and the eluents combined. The solvents (1 liter) were removed by rotary evaporation to yield 5.7 g of solid.

The purified material was taken up in water (300 ml) and washed with dichloromethane (3×200 ml). The aqueous solution was then freeze-dried to give the title compound.

$^1$H NMR (D$_2$O) δ 7.85 (s, 4H, 4× ArH), 5.67, 5.57 (2×d, 2H, J=2.1 Hz, 2×CH), 4.95 (dd, 2H, J=9.0, 1.6 Hz, 2×CH), 4.52 (dd, 2H, J=10.5, 1.6 Hz, 2×CH), 4.42 (dd, 2H, J=9.3, 2.2 Hz, 2×CH), 4.14–4.04 (m, 4H, 4×CH), 3.67 (dd; 2H, J=12, 3 Hz, 2×CH), 3.54–3.44 (m, 6H, 2×CH+2×CH$_2$), 3.21 (t, 4H, J=6.7 Hz, 2×CH$_2$), 1.96 (s, 6H, 2×CH$_3$), 1.85 (m, 4H, 2×CH$_2$).

Microanalysis

Calc: C, 45.02%; H, 6.23%; N, 15.75%. Found: C, 44.80%; H, 6.68%; N, 14.89%.

LC-MS (Method A) showed (M+2H)$^{2+}$=498; T$_{RET}$=1.67 min

EXAMPLE 9

Evaluation of the Compounds of Formula (I)—Inhibition of Influenza Virus Replication Cytopathic effect (CPE) assays were performed essentially as described by Watanabe et al. (J. Virological Methods, 1994 48 257). MDCK cells were infected with a defined inoculum of virus (determined by experimentation to be the minimum sufficient to cause adequate CPE in 72 hours and to be susceptible to control compounds at concentrations considered to be consistent with published norms) in the presence serial dilutions of Compounds of the invention. Cultures were incubated for up to 72 hours at 37° C. in a 5% CO$_2$ atmosphere. The extent of CPE and hence viral replication was determined via metabolism of the viral dye 3-(4,5-dimethylthiazol-2-yl)-2,5-diphenyltetrazolium bromide (MTT) according to published methods (see for example, Watanabe et al., 1994). The compound concentration that inhibited CPE by 50% (ID$_{50}$) was calculated using a computer program for curve fitting. Influenza A/Sydney/5/97 and B/Harbin/7/95 viruses were assayed and the results are shown in Table 2. Comparable data for a specifically disclosed compound in WO 00/55149 and for compound A is also shown in Table 2.

TABLE 2

| Description | ID$_{50}$ µg/ml A/Sydney/5/97+ | ID$_{50}$ µg/ml B/Harbin/7/95 |
|---|---|---|
| Compound A | 0.023 +/− 0.024 | 0.013 +/− 0.011 |
| Compound 2 | 0.0002 | 0.0004 |
| Compound 3 | 0.0001 | 0.00007 |
| Compound 4 | 0.0003 | 0.0004 |
| Compound 5 | 0.0002 | 0.0007 |
| Compound 6 | 0.0002 | 0.0009 |

TABLE 2-continued

| Description | ID$_{50}$ µg/ml A/Sydney/5/97+ | ID$_{50}$ µg/ml B/Harbin/7/95 |
|---|---|---|
| Compound 7 | 0.0007 | 0.0008 |
| Compound 8 | 0.0004 | 0.0009 |
| Compound 9 | 0.0001 | 0.0003 |
| Compound 10 | 0.0002 | 0.0006 |
| Compound 11 | 0.0001 | 0.0001 |
| Compound 12 | >0.1 | 0.0001 |
| Compound 13 | 0.0001 | 0.0003 |
| Compound 14 | 0.0002 | 0.0003 |
| Compound Number 8* | 0.0007, 0.0005 | 0.007 +/− 0.01 |
| Compound Number 10* | 0.057 | >0.1 |

*As referenced in WO 00/55149
+Data provided in WO 00/55149 related to the virus H3N2 isolate A/Victoria/3/75 rather than A H3N2 isolate A/Sydney/5/97. When comparing such data the person skilled in the art will appreciate that differences in antiviral potency are not uncommon for a given compound when analysed against several different viruses in vitro. For example, Woods et al(Antimicrob Agents Chemother 1993 37: 1473–9) have reported that Compound A exhibits a wide range of EC50 values (from 0.02 to 0.16 uM) in in vitro assays involving recent clinical isolates. Accordingly, compound 8 was found to be more potent in CPE assays involving the recent influenza A H3N2 isolate A/Sydney/5/97 than the earlier H3N2 isolate A/Victoria/3/75.

Data provided in Table 2 demonstrate that the compounds 2–14, in addition to being substantially more potent than the highly active compound A, are even more potent against A/Sydney/5/97 and substantially more potent against the recent influenza B isolate B/Harbin/7/95 than compounds 8 and 10 of WO 00/55149.

EXAMPLE 10

Plaque Reduction Assay

Madin Darby Canine Kidney (MDCK) cells are seeded into six well tissue culture plates and grown to confluency via standard methods. Influenza viruses are diluted in a minimal volume of phosphate buffered saline supplemented with 0.2% bovine serum albumin to yield an estimated titre of 50–100 plaque forming units (pfu) per well. After adsorption to the MDCK cells for one hour at 37° C. in a 5% CO$_2$ atmosphere the viral inocula is aspirated and replaced with viral growth media (minimal Eagle's media supplemented with BSA, trypsin and insulin/transferrin/selenium at optimal concentrations) containing sufficient agar or agarose (generally 1–2%) to cause the media to gel at room temperature and at 37° C. in a 5% CO$_2$ atmosphere until plaques develop (generally 2–4 days). Plaques can be visualised with a suitable stain (e.g. 0.4% crystal violet in formal saline) before counting. Antiviral potency is expressed as the concentration of test article which reduces plaque numbers by 50% of the untreated control value (EC$_{50}$).

| | EC$_{50}$ ng/ml PRA | | | | | |
|---|---|---|---|---|---|---|
| Example | A/WSN* | A/Vic* | A/Syd* | A/New* | A/Pan* | A/Bay* |
| Compound A | 56, >100 | 5.5 +/− 8.2 | 2.4 | 0.27, 0.23 | 2.7, 3 | 35 |
| 5 | 0.02 | 0.003 | 0.05 | 0.06 | 0.03 | 0.009 |
| Amantadine | | 220 | | 11 | 157 | |
| Oseltamivir | | 0.11 | | 0.23 | 0.3 | |

*A/WSN/33 BVLV09 (H1N1) A/Victoria/3/75 BVLV017 (H3N2) A/Sydney/5/97 BVLV015 (H3N2) A/New Caledonia/20/99 BVLV008 (H1N1) A/Panama/2007/99 BVLV008 (H3N2) A/Bayern/7/95 BVL006 (H1N1)

| | EC$_{50}$ ng/ml PRA | |
|---|---|---|
| Example | B/HongK* | B/Yam* |
| A | 21 +/− 6 | 0.2, 3.1 |
| 5 | 0.316 | 0.022 |
| Amantadine | >10000 | 2061 |
| Tamlflu | 32 | 0.7 |

*B/Victoria/1/67 B/Hong Kong/5/72 BVLV012 B/Harbin/7/95 BVLV008 B/Yamanashi/166/98 BVLV007

EXAMPLE 11

Assessment of Long Duration of Action

Rodents are anaesthetised and dosed with compound of interest by the intra-tracheal route at a dose volume of 0.8 ml/kg. The rodent is then held in the vertical position until full recovery is achieved. At different time points, for example, 2, 8, 24 and 48 hours post-dose, levels of compound in the lung tissue are assessed by analytical methods. Any analytical method suitable for detection of this type of compound may be used. The time at which levels of compound fall below the sensitivity of the analytical techniques identified will determine the residency time of the compound in lung tissue.

The rat lung retention data for selected compounds is shown below. Please note that all experiments included a co-dosed internal standard, namely compound 3 of International Patent Publication No. WO 02/20514, to permit comparison. The data are expressed as a ratio with respect to this compound, the structure of which is shown below.

Compound 3

The data for compound A is included for comparison purposes. The compounds of the invention have significantly greater retention at 7 days than Compound A when expressed as a ratio of compound concentration to standard concentration.

Rat lung retention assay results

| time point hrs | Compound | dose mg/kg | [cmpd] ng/g | Mean [cmpd] ng/g | [PCT AU01/01128 compound 3] ng/g | Mean [PCT AU01/01128 compound 3] ng/g | Ratio Mean [lung] [cmpd]/PCT AU01/01128 compound 3 |
|---|---|---|---|---|---|---|---|
| 48 | Compound 5 | 0.1 | 1325 | | 1888 | | |
| 48 | Compound 5 | 0.1 | 750 | 951 | 1138 | 1403 | 0.68 |
| 48 | Compound 5 | 0.1 | 778 | | 1184 | | |
| 168 | Compound 5 | 0.1 | 636 | | 1479 | | |
| 168 | Compound 5 | 0.1 | 300 | 403 | 761 | 984 | 0.41 |
| 168 | Compound 5 | 0.1 | 272 | | 712 | | |
| 48 | Compound 1 | 0.1 | 2281 | | 4802 | | |

Rat lung retention assay results

| time point hrs | Compound | dose mg/kg | [cmpd] ng/g | Mean [cmpd] ng/g | [PCT AU01/01128 compound 3] ng/g | Mean [PCT AU01/01128 compound 3] ng/g | Ratio Mean [lung] [cmpd]/PCT AU01/01128 compound 3 |
|---|---|---|---|---|---|---|---|
| 48 | Compound 1 | 0.1 | 650 | 1278 | 1406 | 2874 | 0.44 |
| 48 | Compound 1 | 0.1 | 902 | | 2413 | | |
| 168 | Compound 1 | 0.1 | 280 | | 629 | | |
| 168 | Compound 1 | 0.1 | 611 | 372 | 1568 | 915 | 0.41 |
| 168 | Compound 1 | 0.1 | 227 | | 549 | | |
| 48 | Compound 3 | 0.1 | 2457 | | 4802 | | |
| 48 | Compound 3 | 0.1 | 675 | 1410 | 1406 | 2874 | 0.49 |
| 48 | Compound 3 | 0.1 | 1097 | | 2413 | | |
| 168 | Compound 3 | 0.1 | 245 | | 629 | | |
| 168 | Compound 3 | 0.1 | 544 | 329 | 1568 | 915 | 0.36 |
| 168 | Compound 3 | 0.1 | 199 | | 549 | | |
| 48 | Compound A (zanamivir) | 0.1 | 421 | | 698 | | |
| 48 | Compound A (zanamivir) | 0.1 | 369 | 352 | 1901 | 1368 | 0.26 |
| 48 | Compound A (zanamivir) | 0.1 | 267 | | 1507 | | |
| 168 | Compound A (zanamivir) | 0.1 | 91 | | 815 | | |
| 168 | Compound A (zanamivir) | 0.1 | 47 | 61 | 925 | 750 | 0.08 |
| 168 | Compound A (zanamivir) | 0.1 | 45 | | 512 | | |

EXAMPLE 12

Alternative Assessment of Long Duration of Action and Efficacy

The protocol for infecting mice has been described previously (1–4). Mildly anaesthetised mice are inoculated into the external nares with influenza virus. Treatment procedure and regimen. A single dose of compound is administered at a defined time point up to 10 days prior to infection, preferably 4–7 days prior to infection, or following infection, preferably immediately following infection and up to 48 hours post infection. In most experiments, a non-lethal strain of influenza is used, and efficacy is assessed by reductions in lung virus titre. For mice given compound prior to infection, lungs are removed post infection either on a single day, or on days following infection, preferably days 1–4 post infection. Homogenised lung samples are assayed for virus using established methods, and the titres of viral load estimated and compared to titres of virus in lungs of untreated mice.

In those experiments where a mouse-adapted lethal strain of influenza is used, efficacy is assessed by an increase in survival rate and/or numbers of survivors, as compared to untreated mice.

REFERENCES

1. Ryan, D. M., J. Ticehurst, M. H. Dempsey, and C. R. Penn, 1994. Inhibition of influenza virus replication in mice by GG167 (4-guanidino-2,4-dideoxy-2,3-dehydro-N-acetylneuraminic acid) is consistent with extracellular activity of viral neuramimidase (sialidase). Antimicrob. Agents and Chemother. 38 (10): 2270–2275.

2. von Itzstein M., W.-Y. Wu, G. B. Kok, M. S. Pegg, J. C. Dyason, B. Jin, T. V. Phan, M. L. Smythe, H. F. White, S. W. Oliver, P. M. Colman, J. N. Varghese, D. M. Ryan, J. M. Woods, R. C. Bethell, V. J. Hogham, J. M. Cameron, and C. R. Penn. 1993. Rational design of potent sialidase-based inhibitors of influenza virus replication. Nature (London) 363:418–423.

3. Woods, J. M., R. C. Bethell, J. A. V. Coates, N. Healey, S. A. Hiscox, B. A. Pearson, D. M. Ryan, J. Ticehurst, J. Tilling, S. A. Walcott, and C. R. Penn. 1993. 4-Guanidino-2,4-dideoxy-2,3-dehydro-N-acetylneuraminic acid is a highly effective inhibitor both of the sialidase (neuramimidase) and of growth of a wide range of influenza A and B viruses in vitro. Antimicrob. Agents Chemother. 37:1473–1479.

4. Robert J Fenton, Peter J Morley, Ian J Owens, David Gower, Simon Parry, Lee Crossman and Tony Wong (1999). Chemoprophylaxis of influenza A virus infections, with single doses of zanamivir, demonstrates that zanamivir is cleared slowly from the respiratory tract. Antimicrob. Agents and Chemother. 43, 11, 2642–2647.

What is claimed is:

1. A compound of general formula (I)

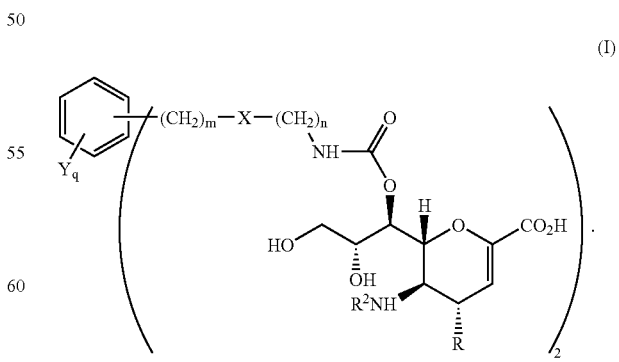

in which

R is an amino or guanidino group;

$R^2$ is acetyl or trifluoroacetyl;

X is CONH, SO$_2$NH, NHCO or NHCONH;
m is either 0 or 1;
n is an integer from 2 to 6;
q is an integer from 0 to 3; and
Y is hydrogen or an aromatic substituent,
or a pharmaceutically acceptable salt, ether, ester or salt of such ester thereof.

2. A compound according to claim 1, in which R is a guanidino group.

3. A compound according to claim 1, in which R$^2$ is an acetyl group.

4. A compound according to claim 1, in which Y is hydrogen, halogen, C$_{1-4}$ alkyl, hydroxy, C$_{1-4}$ alkoxy, amino or carboxy.

5. A compound according to claim 1, which contains a pharmaceutically acceptable salt, ether, ester or salt of such ester at one or more of the carboxyl groups, hydroxyl groups, amino groups or guanidine groups.

6. A compound according to claim 1, in which said compound is an alkyl ester, an aryl ester or an acetyl ester.

7. A method for the preparation of the compound of formula (I) according to claim 1, which comprises the step of deprotecting a compound of formula (II)

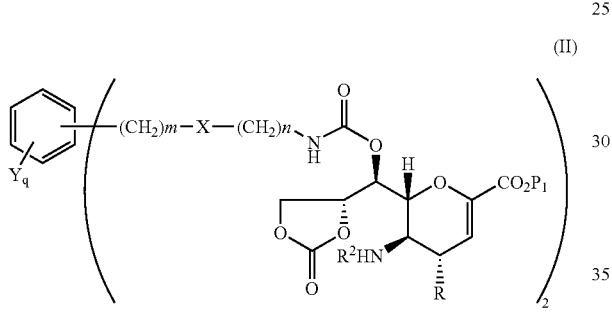

(II)

in which R and R$^2$ are as defined in claim 1 and P$_1$ is a carboxylic acid protecting group.

8. A pharmaceutical formulation comprising a therapeutically effective amount of a compound of formula (I) as defined in claim 1 or a pharmaceutically acceptable salt, ether, ester or salt of such ester thereof, together with one or more pharmaceutically acceptable carriers.

9. A pharmaceutical formulation according to claim 8, which further comprises one or more anti-viral agents used to treat respiratory infections.

10. A pharmaceutical formulation according to claim 9, in which the agent is zanamivir, oseltamivir, amantadine, rimantadine, ribavirin and/or FluVax.

11. An inhaler which comprises a compound according to claim 1.

12. An inhaler according to claim 11 which is adapted for oral administration as a free-flow powder.

13. An inhaler according to claim 11 which is a metered dose aerosol inhaler.

14. A method for the treatment of an orthomyxovirus or paramyxovirus infection, comprising the step of administration to a subject in need thereof of an effective amount of a compound of formula (I) as defined in claim 1.

15. A method according to claim 14 in which the orthomyxovirus or paramyxovirus infection is an influenza A or B infection, parainfluenza, mumps or Newcastle disease.

16. A method according to claim 14 in which the administration is to the respiratory tract by inhalation, insufflation or intranasally or a combination thereof.

17. A method for the preparation of the compound of formula (I) according to claim 1, which comprises the steps of:

(a) reacting a compound of formula (III):

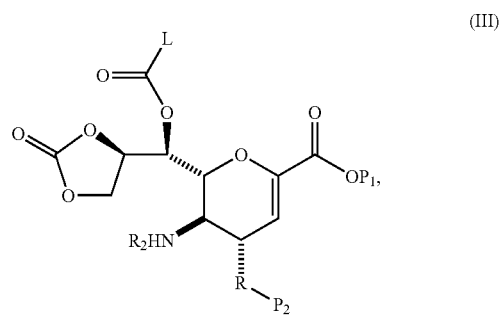

(III)

in which R$_2$ is as defined in claim 1, L is a leaving group, P$_1$ is a carboxylic acid protecting group and P$_2$ is an amine protecting group, with a compound of the compound of formula (IV):

H$_2$N(CH$_2$)$_n$NHP$_2$, (IV)

in which n is defined in claim 1, to form the compound of formula (V):

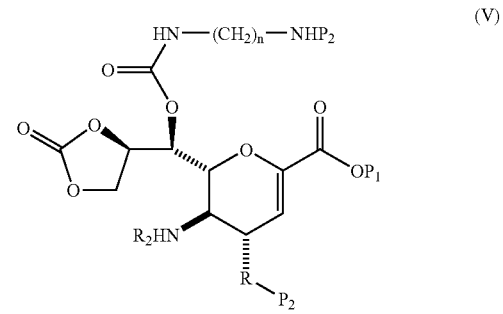

(V)

in which n is defined in claim 1, P$_1$ is a carboxylic acid protecting group and P$_2$ is an amine protecting group, (b) deprotecting the compound of formula (V) to form the compound of formula (VI):

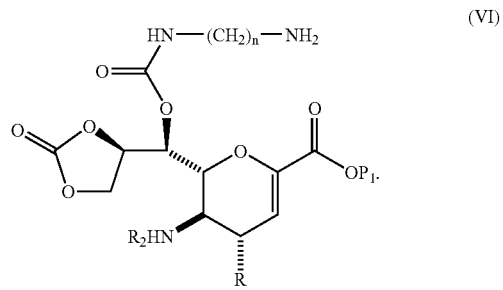

(VI)

(c) reacting the compound of (VI) with a compound of formula (VII) or (VIII):

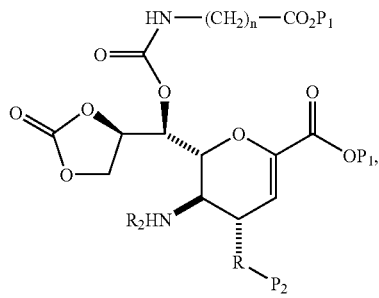

(VII)

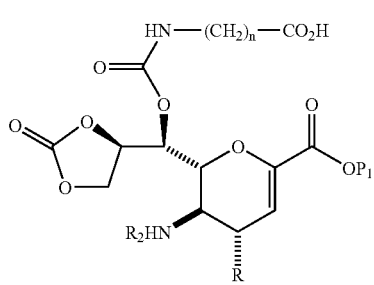

(VIII)

in which m, Y, and q are as defined in claim 1, to form the compound of formula (II):

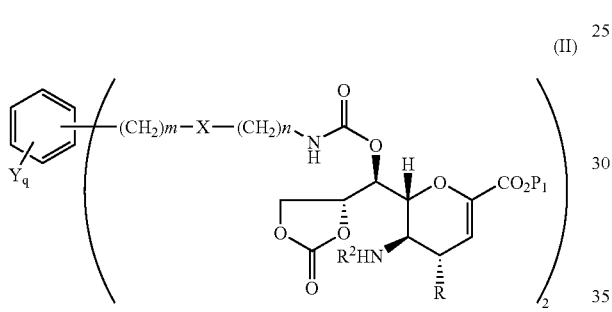

(II)

in which R and R² are as defined in claim 1 and $P_1$ is a carboxylic acid protecting group, and (d) deprotecting the compound of formula (II).

18. A method for the preparation of the compound of formula (I) according to claim 1, which comprises the steps of:

(a) reacting a compound of formula (III):

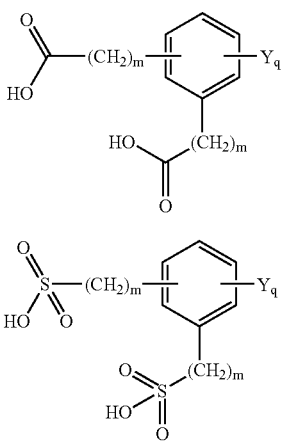

(III)

in which L is a leaving group, $P_1$ is a carboxylic acid protecting group and $P_2$ is an amine protecting group, with a compound of the compound of formula (IX):

$H_2N(CH_2)_nCO_2P_1$, (IX)

in which n is defined in claim 1, to form the compound of formula (X):

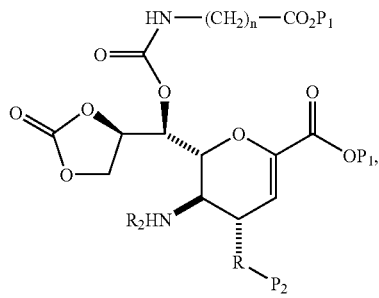

(X)

in which n is defined in claim 1, $P_1$ is a carboxylic acid protecting group and $P_2$ is an amine protecting group, (b) deprotecting a compound of formula (X) to form a compound of formula (XI):

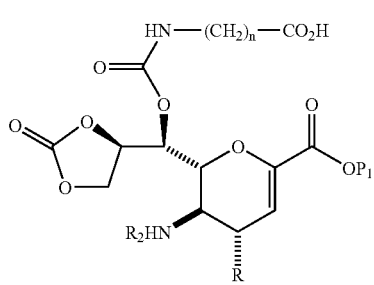

(XI)

(c) reacting the compound of formula (XI) with a compound of formula (XII):

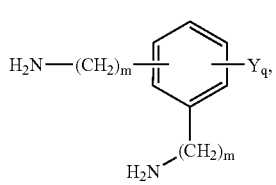

(XII)

in which m, Y, and q are defined in claim 1, to form the compound of formula (II):

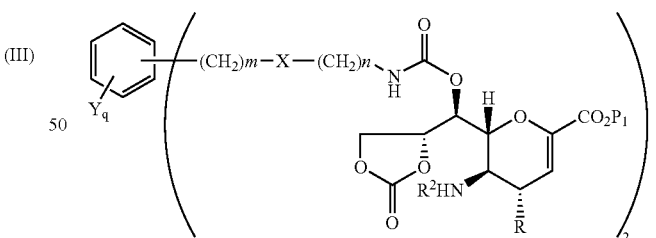

(II)

in which R and R² are as defined in claim 1 and $P_1$ is a carboxylic acid protecting group, and (d) deprotecting the compound of formula (II).

19. A method for the detection of an orthomyxovirus or paramyxovirus infection which comprises the step of contacting the compound of formula (I) as defined in claim 1 with a sample suspected of containing the virus.

20. A method according to claim 14, further comprising the step of administering an effective amount of one or more anti-viral agents used to treat respiratory infections.

* * * * *

UNITED STATES PATENT AND TRADEMARK OFFICE
CERTIFICATE OF CORRECTION

PATENT NO. : 7,157,494 B2  Page 1 of 3
APPLICATION NO. : 10/494243
DATED : January 2, 2007
INVENTOR(S) : Michael D. Dowle et al.

It is certified that error appears in the above-identified patent and that said Letters Patent is hereby corrected as shown below:

In Column 10, Line 45: Please delete "EtOAc ethyl acetate".

In Column 10, Line 47: Please delete "DMF dimethylformamide".

In Column 11, Line 62: Please delete "N-tert-butoxycarbonyl 1,4-diaminobutane" and replace with -- N-tert-butoxycarbonyl-1,4-diaminobutane --.

In Columns 13 and 14, Intermediate 3 compound (on both the top and bottom portions of the page), please delete " 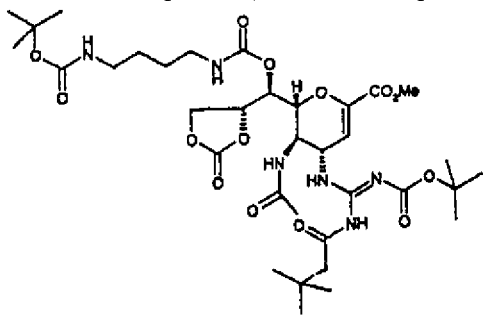 ".

In Columns 13 and 14, Intermediate 3 compound (on both the top and bottom portions of the page), please insert -- 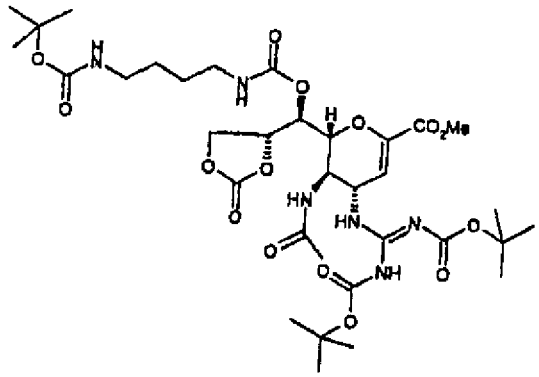 --.

UNITED STATES PATENT AND TRADEMARK OFFICE
CERTIFICATE OF CORRECTION

PATENT NO. : 7,157,494 B2
APPLICATION NO. : 10/494243
DATED : January 2, 2007
INVENTOR(S) : Michael D. Dowle et al.

It is certified that error appears in the above-identified patent and that said Letters Patent is hereby corrected as shown below:

In Column 18, Line 45: Please delete "cyclohexane:EtOAcgave Intermediate" and replace with -- cyclohexane:EtOac gave Intermediate --.

In Column 18, Line 66: Please delete "(green method) $MH^+504$," and replace with -- (green method) $MH^+=504$ --.

In Column 19, Line 20: Please delete "(green method) $MH^+744$," and replace with -- (green method) $MH^+=744$ --.

In Column 19, Line 44: Please delete "(green method) $MH^+488$," and replace with -- (green method) $MH^+=488$ --.

In Column 20, Line 8: Please delete "(green method) $MH^+/2\ 538$," and replace with -- (green method) $MH^+/2=538$ --.

In Column 20, Line 43: Please delete "(green method) $MH^+/2\ 497$," and replace with -- (green method) $MH^+/2=497$ --.

In Column 22 (at the top): Please delete "Intermediate 11".

In Column 25, Line 64: Please delete "0.0357 mmole)," and replace with -- 0.0357 mmol), --.

In Column 25, Line 65: Please delete "0.071 mmole)" and replace with -- 0.0071 mmol) --.

In Column 25, Line 67: Please delete "0.0852 mmole)" and replace with -- 0.0852 mmol) --.

In Column 26, Line 62: Please delete "0.71 mmole)." and replace with -- 0.71 mmol). --.

In Column 30, Line 16, Compound 14: Please delete "1.91 (B, 6H)" and replace with -- 1.91 (s, 6H) --.

In Column 30, Line 27: Please delete "salt (log) of" and replace with -- salt (10g) of --.

UNITED STATES PATENT AND TRADEMARK OFFICE
CERTIFICATE OF CORRECTION

PATENT NO. : 7,157,494 B2
APPLICATION NO. : 10/494243
DATED : January 2, 2007
INVENTOR(S) : Michael D. Dowle et al.

It is certified that error appears in the above-identified patent and that said Letters Patent is hereby corrected as shown below:

In Column 32, Line 20: Please delete "(from 0.02 to 0.16 uM)" and replace with -- from 0.02 to 0.16 μM) --.

In Column 33, Line 8 (in the table): Please delete "Tamlflu" and replace with -- Tamiflu --.

In Columns 33 and 34 (in the chemical structure): Please delete the four instances of the compound "$(CH_2)_5$" and replace with -- $(CH_2)_6$ --.

In Column 35, Line 37: Please delete "Treatment procedure and regimen" and replace with -- Treatment procedure and regimen --.

In Column 38, Claim 17, Line 13: Please delete "$OP_1$," and replace with -- $OP_1$ --.

In Column 38, Claim 17, Line 59: Please delete "$OP_1$," and replace with -- $OP_1$ --.

Signed and Sealed this

First Day of December, 2009

David J. Kappos
*Director of the United States Patent and Trademark Office*